United States Patent
Liu et al.

(10) Patent No.: US 10,967,023 B2
(45) Date of Patent: Apr. 6, 2021

(54) PREPARATION OF A CHINESE MEDICINAL COMPOSITION INCLUDING GINSENG, GINKGO LEAF AND STIGMA CROCI

(71) Applicant: SHINEWAY PHARMACEUTICAL GROUP LTD., Hebei (CN)

(72) Inventors: Jianxun Liu, Beijing (CN); Vivian Zhang, Hebei (CN); Zhigang Li, Hebei (CN); Shyflysky Zhang, Hebei (CN); Xiuwei Guan, Hebei (CN); Iris Lu, Hebei (CN); Weibo Gao, Hebei (CN); Li Xu, Beijing (CN); Wenting Song, Beijing (CN)

(73) Assignee: Shineway Pharmaceutical Group Ltd., Hebei (CN)

( * ) Notice: Subject to any disclaimer, the term of this patent is extended or adjusted under 35 U.S.C. 154(b) by 0 days.

(21) Appl. No.: 16/506,426

(22) Filed: Jul. 9, 2019

(65) Prior Publication Data

US 2019/0328810 A1    Oct. 31, 2019

Related U.S. Application Data

(63) Continuation of application No. 15/540,831, filed as application No. PCT/CN2015/099381 on Jun. 29, 2015, now abandoned.

(30) Foreign Application Priority Data

Dec. 30, 2014 (CN) .......................... 201410840192.7

(51) Int. Cl.
   *A61K 36/258* (2006.01)
   *A61K 36/88* (2006.01)
   *A61K 36/16* (2006.01)

(52) U.S. Cl.
   CPC ............ *A61K 36/258* (2013.01); *A61K 36/16* (2013.01); *A61K 36/88* (2013.01); *A61K 2236/00* (2013.01)

(58) Field of Classification Search
   None
   See application file for complete search history.

(56) References Cited

U.S. PATENT DOCUMENTS

| 8,158,169 B2 * | 4/2012 | Liu .................. A61K 36/88 424/752 |
| 2014/0017219 A1 | 1/2014 | Miller |
| 2016/0199398 A1 | 7/2016 | Gao |

FOREIGN PATENT DOCUMENTS

| CN | 1413656 A | * | 4/2003 |
| CN | 1562186 | | 1/2005 |
| CN | 104491226 A | | 4/2015 |
| JP | 2009534321 A | | 9/2009 |
| WO | 2007118363 A1 | | 10/2007 |

OTHER PUBLICATIONS

Cong, W. et al. Herbal Extracts Combination (WNK) Prevents Decline in Spatial Learning an Memory . . . Evidence Based Complimentary and Alternative Medicine vol. 2012:1-9, 2012. (Year: 2012).*
Zheng Y. et al. Effects and Mechanism of Weinaokang . . . Chinese J Integrative Medicine 16(2)145-150, 2010. (Year: 2010).*
Cong et al., Herbal extracts Combination (WNK) Prevents Decline in Spatial Learning and Memory in APP/PS1Mice through Improvement of Hippocampal Aβ Plaque Formation, Histopathology, and Ultrastructure; Hindawi Publishing Corporation, Evidence-Based Complementary and Alternative Medicine, No. 2012, 9 pages.
Feng et al., Optimization of Extraction of Crocin from Crocus Sativus L. by Orthogonal Regression Design, Chin JMAP, Aug. 2011, vol. 28, No. 8, pp. 729-732.
Liang et al., Rationale and Design of a Multicenter, Phase 2 Clinical Trial to Investigate the Efficacy of Traditional Chinese Medicine SaiLuoTong in Vascular Dementia; Journal of Stroke and Cerebrovascular Diseases, vol. 23, No. 10, 2014, pp. 2626-2364.
Zhang Jun Tian. Modern pharmacology experimental methods. Beijing: Beijing Medical University Press, 1998; pp. 1216-1217.
Zheng, Y., et al., Effects and Mechanism of Weinaokang . . . Chinese J. Integrative Medicine, vol. 16, No. 2, pp. 145-150, 2010.

* cited by examiner

*Primary Examiner* — Ralph J Gitomer
(74) *Attorney, Agent, or Firm* — Stinson LLP

(57) ABSTRACT

Disclosed is a Chinese medicinal composition prepared from the following medical raw materials in parts by weight: 1 part of ginseng, 0.8-1.5 parts of ginkgo leaf and 0.018-0.030 part of stigma croci.

7 Claims, No Drawings

PREPARATION OF A CHINESE MEDICINAL COMPOSITION INCLUDING GINSENG, GINKGO LEAF AND STIGMA CROCI

This application is a continuation application of the U.S. application Ser. No. 15/540,831 filed on Jun. 29, 2017, which is a national phase application of PCT/CN2015/099381, filed on Dec. 29, 2015, which claims priority to CN Application Serial No. 201410840192.7, filed on Dec. 30, 2014, which all are incorporated by reference in their entireties.

TECHNICAL FIELD

The present invention relates to a Chinese medicinal composition for preventing or treating cardiovascular and cerebrovascular diseases or dementia, and it also discloses the preparation method and use of the Chinese medicinal composition.

TECHNICAL BACKGROUND

Cardiovascular and cerebrovascular diseases are the main diseases that threaten people's health and life, and those diseases are characterized in that they have a high morbidity rate, a high mortality rate, a high disability rate and a high recurrence rate. According to the statistical data of recent years, deaths caused by cardiovascular and cerebrovascular disease each year in China accounts for about half of deaths. The popularity of cardiovascular and cerebrovascular disease is closely related to the development of the society and the improvement of the living standards, heavy pressure, irrational diet structure, lack of exercises, excessive tobacco and alcohol consumption, obesity are all causes of cardiovascular and cerebrovascular diseases. Cardiovascular and cerebrovascular diseases include coronary heart disease, angina, myocardial infarction, blood addicted pulmonary heart disease, ischemic encephalopathy, cerebral thrombosis, hypertension, hyperlipidemia and the major reasons to induce these diseases are atherosclerosis, result in vessel stenosis, duct obstruction, thus resulting in insufficient blood supply to the heart and brain, causing heavy head, dizziness, headache, chest tightness and other symptoms, severe cases can lead to stroke and myocardial infarction, cardiovascular ischemia influence energy metabolism, following many changes such as accumulation of lactic acid, calcium overload, free radical injuries. Therefore cardiovascular and cerebrovascular diseases cause serious harm to human health, the early prevention and timely treatment of them has an extremely vital significance.

Dementia is an acquired, sustained intellectual impairment syndrome due to organic brain disorders. Dementia occurs in the elderly is divided into: A. Primary degenerative dementia, namely Alzheimer's disease (AD for short); B. Vascular Dementia (VaD); C. Mixed dementia (AD combined VaD); D. Other dementia (Pick's disease, Lewy inclusions dementia). AD and VaD are the two main types of Dementia.

Vascular dementia is related to one or repeated strokes and high blood pressure, high cholesterol, diabetes, smoking, alcohol consumption and so on, it is manifested as memory, calculation, orientation and judgment disorders, affective disorders and abnormal behavior, even loss of viability when reach to an advanced stage.

Studies suggest that whether cerebral infarction can cause dementia is mainly related to the size, number and location of cerebral infarct lesion. Investigations showed that infarct lesion with the volume of greater than 50 mL can be combined with dementia, with the volume greater than 100 mL are often combined with dementia; investigations also found that, among VaD patients, large area of infarct lesions account for 11.2%, small area of infarct lesions account for 88.8%, multiple lesions accounted for 97.6%, it is mentioned that even when the volume of the lesions are small, dementia can also occur, especially the more the number of infarct lesion, the higher the incidence of dementia. There are also studies suggest that the cerebral infarction site is the key factor leading to dementia; the majority of reports mentioned that the ones with periventricular white matter lesions change found by CT, have significantly increased incidence of dementia. Pavics studied cerebral blood flow changes in patients, and found that for patients with vascular dementia, the average hemispheric blood flow was significantly lower, the perfusion in the infarct area is significantly lower than that of normal tissues, completely non-perfusion areas are rare; studies that compare cognitive scale with cerebral blood flow found that the average hemispheric blood flow was positively correlated to the degree of dementia, suggesting that decrease of VaD blood flow is closely related to intelligence activities. Studies of recent years have noticed that the cerebral blood flow and glucose metabolic rate of some parts, such as the frontal lobe, temporal lobe, especially the thalamus, basal ganglia of VaD patients decreased significantly compared with that of other parts, revealing that VaD might be related to the break of the connections between the cortex and the subcortical structures, i.e. the incomplete connection between the brain nerve function; cerebral vascular resistance, blood viscosity and neurohumoral factors may have a direct or indirect impact on maintaining the cerebral blood flow constant.

Studies have shown that cerebral ischemic injury is a cascade process, and in each sector, different molecular network that cause degeneration damage to neuron is induced; after the occurrence of cerebral infarction, cerebral blood flow interruption and reperfusion happened, cause energy depletion of brain tissue, the increase of neurotransmitter especially excitatory amino acid cause a further decline of blood flow, and flow or release of calcium ions from intracellular calcium stores, cause large amounts of enzymes triggered signal cascades, certain enzymes lead to the generation of oxygen radicals, which themselves also play the role of a second messenger, damage cell proteins, sugars, fatty acids, further cause peri-infarct depolarization, allow the infarct region to expand to penumbra region; free radicals and other messenger activate inflammatory cytokines and enzymes, result in the activation of microglia cells to produce inflammation, thus increase the vascular permeability, damage the neuronal skeleton, while secondary injury results in dementia. Studies have shown that after ischemic condition, neurotransmitters increase first and then decrease, neurotransmitters such as acetylcholine, catecholamine, neuropeptide are closely related to the decline of cognitive ability. They participate in the pathophysiological process of VaD, and may become an important indicator to reflect the severity of VaD.

In recent years, traditional Chinese medicine has shown unique advantages in the treatment of cardiovascular and cerebrovascular diseases, senile dementia, especially vascular dementia, traditional Chinese medicine is effective, lasting, has fewer adverse reactions, are particularly satisfactory in long-term efficacy thus are widely used for the clinic. A lot of researches and clinical practices have proved that traditional Chinese medicine has shown unique advantages as it has a good tolerance and has little side effects, thus it is suitable for long-term use for patients.

Ginseng is warm in nature and has a sweet and slightly bitter flavor, and a function of nourishing the heart and kidney, is good for qi and increase intelligence; Ginkgo leaf is neutral in nature and has a bitter and astringent flavor, and has a function of promoting blood circulation to remove blood stasis. Stigma croci is neutral in nature, and has a sweet flavor, and has a function of promoting blood circulation to remove blood stasis, dissipating blood stasis and knots. Modern pharmacological studies have confirmed that ginseng contains a variety of saponins which can significant improve the cerebral ischemia reperfusion injury and memory impairment in learning of many experimental animals, they can improve the ability of learning and memory in normal animals, and have effects of increasing the uptake of neurotransmitter of synaptosomes and enhancing the nerve growth factor; Ginkgo leaf extract can inhibit the peroxidation of cell membrane lipid, and can dilate blood vessels, increase blood flow, reduce blood viscosity, inhibit thrombosis and has an effect of anti-platelet aggregation, improving cerebral metabolism, protecting the nervous cells; stigma croci has effects of inhibiting the influx of extracellular calcium and the release of calcium from endoplasmic reticulum, anti-oxidation, anti-hypertension, atherosclerosis, cerebral edema etc., it can also improve the partial pressure of the oxygen in the blood flow of mammals, in recent years, it has also been found that it has the anti-alcohol induced impairment of memory and learning effect.

Patent ZL02131435.7 discloses a Chinese medicinal composition containing a therapeutically effective amount of a ginseng, ginkgo leaf and stigma croci for the treatment of ischemic cerebrovascular disease and vascular dementia, senile dementia diseases and so on. Based on the above patent, the patent applicant developed the "Sailuotong Capsule" (its original trade name is "Weinaokang"), currently it is in clinical trials.

Patent WO2007118363A1 discloses a similar Chinese medicinal composition for the treatment of ischemic cerebrovascular disease and senile dementia, and it is made of ginseng, ginkgo leaf, stigma croci and soybean.

When studying the above-mentioned patents systematically, the inventor has found that better results can be achieved when using specific composition of components and content ratio.

SUMMARY OF THE INVENTION

The inventors have conducted a systematic experimental study for the effects of the components of the compositions mentioned in the patent ZL02131435.7 and WO2007118363A1 for preventing or treating cardiovascular and cerebrovascular diseases and dementia and found that the effect of soybean in the composition is not obvious. Through the optimization study of the prescription, the inventors have found that a pharmacological effect that is better than that of the composition of WO2007118363A1 can be achieved by only using the three ingredients of Chinese medicine: ginseng, ginkgo leaf and stigma croci.

In addition, the inventors have also found that a composition that is made with specific weight ratio of ginseng, ginkgo leaf and stigma croci have better effects of treating or preventing cardiovascular and cerebrovascular diseases and dementia, especially in the treatment of ischemic cerebrovascular disease, coronary heart disease, angina, and senile dementia, particularly it has a better effect on the treatment of vascular dementia diseases. According to the study, the doses of the composition made of ginseng, ginkgo leaf and stigma croci in the medicine can be further reduced, the energy can thus be saved and the cost can be reduced, and the side effects generated by long-term consumption of the composition can be further reduced.

Therefore, the object of the present invention is to provide a Chinese medicinal composition for the prevention or treatment of cardiovascular disease or dementia with a better effect and the preparation method and use thereof.

The object of the present invention is achieved by the following technical solutions:

A Chinese medicinal composition for preventing or treating cardiovascular and cerebrovascular disease or dementia, the raw material that makes the Chinese medicinal composition is the medicine with the following weight ratio of ingredients:

1 part of ginseng, 0.8-1.5 parts of ginkgo leaf, 0.018-0.030 part of stigma croci.

Preferably, the raw material that makes the Chinese medicinal composition is the medicine with the following weight ratio of ingredients:

1 part of ginseng, 1 part of ginkgo leaf, 0.018-0.030 part of stigma croci.

More preferably, the raw material that makes the Chinese medicinal composition is the medicine with the following weight ratio of ingredients:

1 part of ginseng, 0.9-1.2 parts of ginkgo leaf, 0.020-0.025 part of stigma croci.

Still more preferably, the raw material that makes the Chinese medicinal composition is the medicine with the following weight ratio of ingredients:

1 part of ginseng, 1 part of ginkgo leaf, 0.020-0.025 part of stigma croci.

Most preferably, the raw material that makes the Chinese medicinal composition is the medicine with the following weight ratio of ingredients:

1 part of ginseng, 1 part of ginkgo leaf, 0.022 part of stigma croci.

The present invention also provides a method for preparing the above Chinese medicinal composition.

The Chinese medicinal composition of the present invention can be prepared by a variety of methods.

In one embodiment of the present invention, weighing the three Chinese medicines: ginseng, ginkgo leaf and stigma croci according to the above ratio, mixing then grinding or grinding then mixing to obtain the composition.

In another embodiment of the present invention, weighing the three Chinese medicines: ginseng, ginkgo leaf and stigma croci according to the above ratio, mixing then extracting to prepare the composition.

In a preferred embodiment of the present invention, the preparation method of the Chinese medicinal composition comprises the following steps: the step of weighing the three Chinese medicines: ginseng, ginkgo leaf and stigma croci according to the above ratio, the step of preparing ginseng extract, the step of preparing ginkgo leaf extract, the step of preparing stigma croci extract, the step of mixing the above ginseng extract, the ginkgo leaf extract and the stigma croci extract.

Preferably, in the step of the preparing ginseng extract, the main component obtained is total ginsenosides; in the step of preparing Ginkgo leaf extract, the main component obtained is Ginkgo leaf total flavonoids and total lactones; in the step of preparing stigma croci extract, the main component obtained is stigma croci total glycosides.

Extracts of the three above-mentioned components can be prepared by conventional extraction methods for extracting the above components, the preparation method of the components by extraction is mature, such as the total ginsenosides, the Ginkgo leaf total flavonoids and total lactones can be prepared by extraction methods recorded in the pharmacopeia, the extraction method of the stigma croci total glycosides can adopt the extraction method recorded in the literature "Chinese modern applied Pharmacy" (August 2011, Vol. 28 No. 8, page 729-731).

In one embodiment of the present invention, the method for preparing the ginseng extract is as follows: the ginseng is grinded into powders, then it is subjected to reflux extraction with ethanol for 2 times, it is filtered, the filtrate is decompressed to recover the solvent until the relative density is 1.12-1.14 at 70° C., water with the amount that equals to 2-6 times of that of crude drug is added for stirring homogeneously, then it is cooled for precipitation, the supernatant is loaded onto a macroporous adsorptive resin, the resin that carries drug is washed with distilled water first, then is eluted with ethanol, the ethanol eluent is collected and concentrated until dry to obtain the ginseng extract.

In one embodiment of the present invention, the method for preparing the Ginkgo leaf extract is as follows: warm ethanol is added to Ginkgo leaf coarse powder for immersion, the powder is filtered and the filter residue is immersed with warm ethanol, then is filtered, the filtrate of the two times of immersion are combined, concentrated under reduced pressure until the relative density is 1.12-1.14 at 70° C., water with the amount that equals to 2-6 times of that of crude drug is added, it is stirred homogeneously, then it is cooled for precipitation, filtered, the filtrate is loaded onto a macroporous adsorptive resin, the resin that carries drug is washed with distilled water first, then is eluted with ethanol, the ethanol eluent is collected and concentrated until the relative density is 1.02-1.04 at 70° C., it is extracted by ethyl acetate:n-butyl alcohol, the extracts are combined and are decompressed to recover solvent to obtain Ginkgo leaf extract.

In one embodiment of the present invention, the method for preparing the stigma croci extract is as follows: cold ethanol is added into stigma croci crude drug for immersion, then it is filtered, cold ethanol is added to the residues for immersion, then it is filtered, the filtrate of the two times of immersion are combined, concentrated under reduced pressure until the relative density is 1.12-1.14 at 70° C., water is added, then it is loaded onto a macroporous adsorptive resin, the resin that carries drug is washed with distilled water first, then is eluted with ethanol, the ethanol eluent is concentrated until the relative density is 1.02-1.04 at 70° C., it is concentrated until dry to obtain stigma croci extract.

The present invention also provides a Chinese medicinal formulation for preventing or treating cardiovascular and cerebrovascular diseases and/or dementia which is composed of the above Chinese medicinal composition and at least one pharmaceutically acceptable excipient.

The formulation may be a solid formulation or a semi-solid formulation, liquid formulation or gaseous formulation.

The solid or semi-solid formulation is selected from one of the following formulations: tablets, pills, ointments, sublimed preparations, pulvis, granules, suppositories, powders, emulsions, chewables, capsules.

The liquid formulation is selected from one of the following formulations: oral liquid, suspensions, syrups, injections, medicinal liquor and tinctures.

The gaseous preparation is aerosol or inhalation.

The present invention also provides use of a Chinese medicinal composition or formulation in the prevention or treatment of cardiovascular and cerebrovascular diseases and/or dementia.

Preferably, the cardiovascular and cerebrovascular disease is selected from at least one of the following diseases: ischemic cerebrovascular disease, coronary heart disease or angina.

Preferably, the dementia is selected from senile dementia, especially vascular dementia.

Compared with the prior art, the Chinese medicinal composition of the present invention has the following technical effects:

(1) The Chinese medicinal compositions and formulations of the present invention are more effective in the prevention or treatment of the cardiovascular and cerebrovascular disease or dementia.

(2) The amount of the Chinese medicinal composition of the present invention in a medicine is lower, and thus save costs and energy.

(3) The side effects of the Chinese medicinal composition of the present invention is small, and the composition has good safety performance, thus can be used for long-term, and has a good prospect for used in medicine

EMBODIMENTS

The present invention will be further illustrated with the combination of the following examples, comparative examples and related test examples, however, these examples and test examples shall only be used to illustrate the present invention but not limit the extent of the present invention. In the following examples and test examples, the experiment methods without specific experiment conditions are carried out in accordance with conventional conditions, or in accordance with the conditions that are recommended by the manufacturers.

Part 1: Preparation of the Chinese Medicinal Composition and Formulation of the Present Invention Example 1

| | |
|---|---|
| ginseng | 1 part |
| ginkgo leaf | 0.8 part |
| stigma croci. | 0.018 part |

Ginseng extract, ginkgo leaf extract, stigma croci extract were obtained respectively according to the methods disclosed in example 1 of Patent ZL02131435.7, the three extracts were mixed and were further prepared to granules, capsules and injections according to conventional methods.

Example 2

| | |
|---|---|
| ginseng | 1 part |
| ginkgo leaf | 1.5 parts |
| stigma croci. | 0.030 part |

The mixture of the extracts and the preparation were prepared according to the methods of the example 1 of the present invention.

Example 3

| | |
|---|---|
| ginseng | 1 part |
| ginkgo leaf | 1 part |
| stigma croci. | 0.018 part |

The mixture of the extracts and the preparation were prepared according to the methods of the example 1 of the present invention.

Example 4

| | |
|---|---|
| ginseng | 1 part |
| ginkgo leaf | 1 part |
| stigma croci. | 0.030 part |

The mixture of the extracts and the preparation were prepared according to the methods of the example 1 of the present invention.

Example 5

| | |
|---|---|
| ginseng | 1 part |
| ginkgo leaf | 0.9 part |
| stigma croci. | 0.020 part |

The mixture of the extracts and the preparation were prepared according to the methods of the example 1 of the present invention.

Example 6

| | |
|---|---|
| ginseng | 1 part |
| ginkgo leaf | 1.2 parts |
| stigma croci. | 0.025 part |

The mixture of the extracts and the preparation were prepared according to the methods of the example 1 of the present invention.

Example 7

| | |
|---|---|
| ginseng | 1 part |
| ginkgo leaf | 1 part |
| stigma croci. | 0.20 part |

The mixture of the extracts and the preparation were prepared according to the methods of the example 1 of the present invention.

Example 8

| | |
|---|---|
| ginseng | 1 part |
| ginkgo leaf | 1 part |
| stigma croci. | 0.025 part |

The mixture of the extracts and the preparation were prepared according to the methods of the example 1 of the present invention.

Example 9

| | |
|---|---|
| ginseng | 1 part |
| ginkgo leaf | 1 part |
| stigma croci. | 0.022 part |

Ginseng extract and ginkgo leaf extract were extracted according to the methods recorded in Chinese pharmacopoeia (2010 edition, part one), page 367-368 and page 392-393 respectively, stigma croci extract was extracted according to the method recorded in the literature "Chinese Modern Applied Pharmacy" (August 2011 Vol. 28 the eighth, pages 729-731), the three extracts were mixed and were further prepared to granules, capsules and injections according to conventional methods.

Example 10

| | |
|---|---|
| ginseng | 1 part |
| ginkgo leaf | 0.8 part |
| stigma croci. | 0.030 part |

The mixture of the extracts and the preparation were prepared according to the methods of the example 9 of the present invention.

Example 11

| | |
|---|---|
| ginseng | 1 part |
| ginkgo leaf | 1.5 parts |
| stigma croci. | 0.018 part |

The mixture of the extracts and the preparation were prepared according to the methods of the example 9 of the present invention.

Example 12

| | |
|---|---|
| ginseng | 1 part |
| ginkgo leaf | 0.9 part |
| stigma croci. | 0.025 part |

The mixture of the extracts and the preparation were prepared according to the methods of the example 9 of the present invention.

Example 13

| | |
|---|---|
| ginseng | 1 part |
| ginkgo leaf | 1.2 parts |
| stigma croci. | 0.02 part |

The mixture of the extracts and the preparation were prepared according to the methods of the example 9 of the present invention.

Part 2: Preparation of the Chinese Medicinal Composition and Formulation of the Comparative Examples Comparative Example 1

| | |
|---|---|
| ginseng | 1 part |
| ginkgo leaf | 1 part |
| stigma croci. | 0.1 part |

The mixture of the extracts and the preparation were prepared according to the methods of the example 1 of the present invention.

Comparative Example 2

| | |
|---|---|
| ginseng | 1 part |
| ginkgo leaf | 1 part |
| stigma croci. | 0.015 part |

The mixture of the extracts and the preparation were prepared according to the methods of the example 1 of the present invention.

Comparative Example 3

| | |
|---|---|
| ginseng | 1 part |
| ginkgo leaf | 1.5 parts |
| stigma croci. | 0.4 part |

The mixture of the extracts and the preparation were prepared according to the methods of the example 1 of the present invention.

Comparative Example 4

| | |
|---|---|
| ginseng | 1 part |
| ginkgo leaf | 1.9 parts |
| stigma croci. | 0.05 part |

The mixture of the extracts and the preparation were prepared according to the methods of the example 9 of the present invention.

Comparative Example 5

The extract mixture and the corresponding formulation were prepared according to the composition and the preparation method of example 1 of the Patent ZL02131435.7.

Comparative Example 6

The extract mixture and the corresponding formulation were prepared according to the composition and the preparation method of example 2 of the Patent ZL02131435.7.

Comparative Example 7

The extract mixture and the corresponding capsules were prepared according to the prescription of the composition and the preparation method of example 1 of the Patent WO2007/118363.

Comparative Example 8

The extract mixture and the corresponding capsules were prepared according to the prescription of the composition of example 2 of the Patent WO2007/118363 and the preparation method of example 1 of the Patent WO2007/118363.

PART 3 PHARMACODYNAMIC EXPERIMENTS

Test Example 1

Protection to the Ischemic Myocardium of the Experimental Rats Experimental Materials Healthy male Wastar rats, weight 180~220 g, clean grade, provided by Vital River Animal Experiment Center.

Chinese medicinal composition of the present invention and Chinese medicinal composition of comparative examples (self-made, the mixture of the three extracts were prepared according to the methods of the examples and comparative examples of the present invention), were prepared to 0.15 g/mL with distilled water during the experiment (calculated based on the original dose of the Chinese medicinal composition).

Reagents: urethane, isoproterenol hydrochloride, sodium chloride injection, CK, CK-MB kit.

Instruments: physiological recorder BL-420 physiological signal acquisition system, centrifuges, semi-automatic biochemical analyzer.

Experiment Methods a) Grouping and Model Preparation:

Before the test and before giving medicine, ran ECG examination for the rats, discarded the S-T segment, there were abnormal changes and abnormal heart rhythms in T wave. The rats were randomly divided into blank control group and model group, 10 rats in each group, each rate received a gavage respectively each day: saline was given to the blank group, the group of the Chinese medicinal composition of the present invention (Example 1, Example 2, Example 5, Example 6, Example 9, Example 11, were given according to a dose of 3 g/kg/d, the dose was calculated based on the original dose of ginseng, ginkgo leaf and stigma croci), the group of the comparative examples (wherein, comparative example 1, comparative example 2, comparative example 3, comparative example 4, comparative example 5, comparative example 6 were given medicines according to a dose of 3 g/kg/d, the dose was calculated based on the original dose of ginseng, ginkgo leaf, stigma croci; comparative example 7, comparative example 8 were given medicines according to a dose of 3 g/kg/d, wherein the dose was calculated based on the original dose of ginseng, ginkgo leaf, stigma croci, soybean), the medicine was administered continuously for 10 days, in the 10th day, 30 min after the perfusion, a model was created according to the following method: 5 ml/kg20% urethane was given to the rats of each group through intraperitoneal injection, after the rats were light anesthetized, the backs of the rats were fixed, isoproterenol hydrochloride was injected through multiple points subcutaneously, the equal volume of saline was given to the normal control group, the ECG machines was connected, the speed for the paper to move is 50 cm/s, the standard voltage was 10 mm/mv, the ECG change after modeling was recorded. ECG was lead, the changes of ST segment were observed. One of the following conditions were considered to be positive for myocardial ischemia: 1) in S-T segment, an upward or downward horizontal shift≥0.1 mv; 2) T-wave is higher than ½ of the R wave that was led; 3) T-wave was high and there's a displacement in S-T segment. The standard for the ones that are negative: 1) in S-T segment, oblique shift or horizontal shift<0.1 mv; 2) T wave was flat and low or inverted in the two directions. An elevation in ST segment≥0.1 mv of the ECG of the rats in the modeling group is considered to be a sign of success modeling.

b) Experiment Methods:

Continuous administration for 10 days, 30 min after the last gavage, a model was created, ECG was lead using physiological recorder immediately, 5 min, 10 min, 20 min, 30 min before modeling and after modeling, and blood collection was carried out after 6 h, serum was collected after centrifugation, run CK, CK-MB.

c) Statistical Analysis:

Experimental data were expressed by mean±standard deviation, t test was used for statistical analysis.

3 Results a) Effects on the J Point Displacement

There were significant differences between the blank group and the model group (P<0.01); compared with the model group, the groups of the Chinese medicinal compositions of the present invention had significant decreasing effects for the J point displacement at different time (P<0.05~0.01), and the effects of the Chinese medicinal compositions were better than each of the comparative groups. See Table 1.

b) The Effects on the CK, CK-MB of the Serum of Isoproterenol Induced Acute Myocardial Ischemia Rats Compared with the blank group, the Chinese medicinal compositions of the present invention had very significant differences; compared with the model group, 6 h after modeling, the creatine kinase CK, the creatine kinase isoenzyme CK-MB were significantly reduced; and compared with the comparative group, the effects of the compositions of the present invention were better. The Chinese medicinal compositions of the present invention showed a better protection to the isoproterenol induced myocardial ischemia injury of rats. See Table 2.

TABLE 2

Effects on the CK, CK-MB of the serum of isoproterenol induced acute myocardial ischemia rats ($X \pm \bar{S}$, n = 10)

| Groups | dose (g/kg) | CK (U/L) | CK-MB (U/L) |
|---|---|---|---|
| Blank group | — | 336.27 ± 40.01** | 205.27 ± 36.33** |
| Model group |  | 1465.44 ± 235.18 | 815.44 ± 125.18 |
| Example 1 | 3 | 392.27 ± 18.12** | 277.47 ± 33.02** |
| Example 2 | 3 | 402.57 ± 32.15** | 282.59 ± 32.11** |
| Example 5 | 3 | 410.32 ± 30.18** | 264.32 ± 29.63** |
| Example 6 | 3 | 425.04 ± 20.42** | 277.47 ± 27.32** |
| Example 9 | 3 | 387.59 ± 19.71** | 252.59 ± 41.31** |
| Example 11 | 3 | 420.32 ± 34.38** | 264.32 ± 31.13** |
| Comparative example 1 | 3 | 675.02 ± 37.12* | 575.02 ± 52.32* |
| Comparative example 2 | 3 | 560.98 ± 49.28* | 360.98 ± 31.05* |
| Comparative example 3 | 3 | 678.02 ± 42.12* | 475.02 ± 52.32* |
| Comparative example 4 | 3 | 860.98 ± 41.27* | 560.98 ± 45.41* |

TABLE 1

Effects of the Chinese medicinal compositions of the present invention on J point displacement of rats ($X \pm \bar{S}$, n = 10)

| groups | dose (g/kg) | Before modeling | 5 min after modeling | 10 min after modeling | 20 min after modeling | 30 min after modeling |
|---|---|---|---|---|---|---|
| Blank group | — | 0.19 ± 0.02 | 0.21 ± 0.01** | 0.21 ± 0.04** | 0.21 ± 0.02** | 0.21 ± 0.03** |
| Model group |  | 0.19 ± 0.01 | 0.43 ± 0.02 | 0.45 ± 0.03 | 0.47 ± 0.02 | 0.47 ± 0.04 |
| Example 1 | 3 | 0.19 ± 0.02 | 0.40 ± 0.03 | 0.38 ± 0.02* | 0.31 ± 0.03** | 0.22 ± 0.02** |
| Example 2 | 3 | 0.20 ± 0.02 | 0.39 ± 0.02* | 0.39 ± 0.03* | 0.29 ± 0.04** | 0.24 ± 0.01** |
| Example 5 | 3 | 0.19 ± 0.03 | 0.40 ± 0.02 | 0.36 ± 0.03* | 0.31 ± 0.04** | 0.25 ± 0.02** |
| Example 6 | 3 | 0.19 ± 0.01 | 0.40 ± 0.03 | 0.38 ± 0.02* | 0.30 ± 0.03** | 0.26 ± 0.02** |
| Example 9 | 3 | 0.19 ± 0.02 | 0.39 ± 0.02* | 0.39 ± 0.03* | 0.29 ± 0.02** | 0.23 ± 0.03** |
| Example 11 | 3 | 0.20 ± 0.02 | 0.40 ± 0.01 | 0.36 ± 0.03* | 0.31 ± 0.04** | 0.26 ± 0.05** |
| Comparative example 1 | 3 | 0.20 ± 0.03 | 0.43 ± 0.04 | 0.40 ± 0.04* | 0.35 ± 0.02* | 0.32 ± 0.04* |
| Comparative example 2 | 3 | 0.19 ± 0.02 | 0.41 ± 0.03 | 0.39 ± 0.04* | 0.34 ± 0.03* | 0.32 ± 0.02* |
| Comparative example 3 | 3 | 0.19 ± 0.03 | 0.42 ± 0.02 | 0.40 ± 0.03* | 0.34 ± 0.04* | 0.37 ± 0.04* |
| Comparative example 4 | 3 | 0.19 ± 0.01 | 0.42 ± 0.01 | 0.39 ± 0.03* | 0.35 ± 0.02* | 0.35 ± 0.05* |
| Comparative example 5 | 3 | 0.20 ± 0.03 | 0.43 ± 0.02 | 0.42 ± 0.03 | 0.39 ± 0.04* | 0.37 ± 0.04* |
| Comparative example 6 | 3 | 0.19 ± 0.02 | 0.43 ± 0.02 | 0.42 ± 0.03 | 0.41 ± 0.01* | 0.40 ± 0.03* |
| Comparative example 7 | 3 | 0.20 ± 0.01 | 0.43 ± 0.03 | 0.38 ± 0.02* | 0.33 ± 0.01* | 0.26 ± 0.03** |
| Comparative example 8 | 3 | 0.19 ± 0.02 | 0.42 ± 0.04 | 0.41 ± 0.03 | 0.39 ± 0.05* | 0.39 ± 0.03* |

PS: compared with the model group,
*P < 0.05;
**P < 0.01

TABLE 2-continued

Effects on the CK, CK-MB of the serum of isoproterenol induced acute myocardial ischemia rats ($X \pm \overline{S}$, n = 10)

| Groups | dose (g/kg) | CK (U/L) | CK-MB (U/L) |
|---|---|---|---|
| Comparative example 5 | 3 | 946.52 ± 56.04* | 674.52 ± 57.78 |
| Comparative example 6 | 3 | 1073.41 ± 35.12 | 713.41 ± 40.72 |
| Comparative example 7 | 3 | 489.41 ± 65.27* | 343.17 ± 26.04* |
| Comparative example 8 | 3 | 861.31 ± 52.74* | 591.31 ± 37.01* |

PS: compare with the model group,
*P < 0.05;
**P < 0.01

Summary: myocardial ischemia refers to a pathological state with the reduction of the blood perfusion of hearts, resulting in the reduction of oxygen supply of hearts, the abnormal myocardial energy metabolism, the normal work of heart not being supported. Coronary heart disease is the main cause and the most common cause of myocardial ischemia. Compared with the Chinese medicinal compositions of the comparative examples, for the isoproterenol induced myocardial ischemia rats, the Chinese medicinal compositions of the present invention can significantly decrease the J point displacement at different time (P<0.05~0.01), can significantly decrease serum CK, CK-MB, which shows that the Chinese medicinal compositions of the present invention have a significant protection to the myocardial ischemia, and the effects thereof are better than that of the Chinese medicinal composition of the comparative example.

Test Example 2

Lipid-Lowering Experiments

Experimental Materials

Kunming mice, weight 18~22 g, half male and half female, provided by Vital River Animal Experiment Center.

Chinese medicinal compositions of the present invention and Chinese medicinal compositions of the comparative examples (self-made, the mixture of the corresponding extracts were prepared according to the methods of the examples and comparative examples of the present invention), were prepared to 0.2 g/mL with distilled water during the experiment (calculated based on the original dose of the composition).

Reagents: total cholesterol (TC) test kit; triglyceride (TG) assay kit.

Instrument: B-260 type thermostat water bath; TDL 80-2B type low-speed centrifuge; THER-MO LABSYSTEM MK3 type microplate reader.

Experiment Methods

Take Kunming mice, they were randomly divided into a control group (16), a high fat model group (16), the groups of the compositions of the present invention (10 for each group), the groups of the comparative examples (10 for each group), in each group, half male and half female. Normal control group was fed with normal diet, the other groups were fed with high-fat diet (the ingredients were as follows: 77.5% base diet, 2% cholesterol, 10% lard, 10% egg yolk powder, 0.5% sodium deoxycholate). Mice were weighed once a week, were fed five weeks. Five weeks later, 3 male and female mice were randomly taken from the normal compare group and the high fat model group, the eyeballs were taken to collect blood, serum TC and TG were measured. The serum TC and TG of the normal compare group were lower than that of the high fat model group, the differences of the data were significant, indicating that the hyperlipemia mice model were created, the mice can be used for formal testing. Then a equal volume of perfusion were given to the stomach of the mice of each group according to the dose mentioned in table 4 (wherein, the Chinese medicinal composition of the present invention (Example 1, Example 2, Example 5, Example 6, Example 9, Example 11, were administered according to a dose of 4 g/kg/d, the dose was calculated according to the original dose of ginseng, ginkgo leaf, stigma croci), comparative group (wherein, comparative example 1, comparative example 2, comparative example 3, comparative example 4, comparative example 5, comparative example 6 were administered according to a dose of 4 g/kg/d, the dose was calculated based on the original dose of ginseng, ginkgo leaf, stigma croci; comparative example 7, comparative example 8 were administered according to a dose of 3 g/kg/d, the dose was calculated according to the original dose of ginseng, ginkgo bleaf, stigma croci and soybean). The medicine of each group were prepared into suspension with 1% sodium carboxymethyl cellulose. After 3 weeks of administration, all animals were fasted for 12 h, weighed, and the eyeballs were removed to collect blood, the blood samples were centrifuged at 3000 rpm for 10 min, the serums were separated, the operation was carried out according to the instruction of the total cholesterol and triglycerides kit, TC and TG were measured. The resulting data were counted with SPSS10.0 statistical software, the data were expressed with $\overline{X} \pm S$.

Results a) The Effects of the Medicine of Each Group on the Increase of Weight of the High Lipid Mice At the beginning of the experiment, the body weight of the mice of each group were about 18-20 g, after a five-week high fat diet modeling, the body weight changes of mice in each group are different. It can be seen: compared with the normal control group, the changes of the weight of the high fat model group, the group of the compositions of the present invention, the group of the comparative examples are significantly increased, after 3 weeks of administration, the weight of the model group are increased to the highest, indicating the high lipid model group is kept, the Chinese medicinal compositions of the present invention and the Chinese medicinal compositions of the comparative examples can all significantly decrease the weight of the animals in the high fat model group (P<0.05). And the medicinal compositions of the present invention had a better effect on decreasing weight. See table 3.

TABLE 3

Effects of the Chinese medicinal compositions of the present invention on the weight of the mice (g)

| Groups | Dose (g/kg) | Day 0 | Day 7 | Day 14 | Day 21 | Day 28 |
|---|---|---|---|---|---|---|
| Blank group | | 19.81 ± 0.57 | 20.26 ± 1.11 | 21.67 ± 0.83 | 22.17 ± 0.96 | 23.11 ± 0.69 |
| Model group | | 19.55 ± 0.94 | 20.45 ± 1.29 | 21.52 ± 1.01 | 22.57 ± 1.17 | 25.62 ± 1.14 |

TABLE 3-continued

Effects of the Chinese medicinal compositions of the present invention on the weight of the mice (g)

| | | | | | | |
|---|---|---|---|---|---|---|
| Example 1 | 4 | 19.24 ± 0.85 | 20.21 ± 0.91 | 21.37 ± 1.19 | 22.27 ± 0.74 | 24.31 ± 1.01 |
| Example 2 | 4 | 20.07 ± 0.52 | 20.67 ± 1.24 | 21.78 ± 1.15 | 23.11 ± 0.85 | 25.21 ± 0.92 |
| Example 5 | 4 | 20.42 ± 0.77 | 20.73 ± 0.87 | 21.61 ± 1.30 | 23.51 ± 0.94 | 24.13 ± 1.34 |
| Example 6 | 4 | 19.78 ± 0.60 | 20.56 ± 1.31 | 21.37 ± 1.12 | 22.34 ± 0.92 | 24.61 ± 1.17 |
| Example 9 | 4 | 20.85 ± 0.59 | 20.38 ± 1.15 | 21.44 ± 0.87 | 23.29 ± 1.27 | 24.51 ± 0.83 |
| Example 11 | 4 | 20.37 ± 0.69 | 20.87 ± 1.07 | 21.21 ± 1.02 | 22.86 ± 1.08 | 25.13 ± 1.14 |
| Comparative example1 | 4 | 19.77 ± 0.84 | 20.65 ± 0.77 | 22.08 ± 1.15 | 23.01 ± 1.14 | 25.61 ± 1.11 |
| Comparative example2 | 4 | 20.13 ± 0.91 | 20.91 ± 1.28 | 21.61 ± 1.01 | 22.74 ± 0.76 | 25.51 ± 0.92 |
| Comparative example 3 | 4 | 19.84 ± 0.67 | 20.41 ± 1.18 | 21.77 ± 1.07 | 23.48 ± 1.24 | 25.13 ± 1.27 |
| Comparative example 4 | 4 | 20.27 ± 0.57 | 19.74 ± 1.21 | 21.78 ± 1.05 | 23.95 ± 1.12 | 25.78 ± 1.16 |
| Comparative example 5 | 4 | 19.42 ± 1.03 | 19.74 ± 0.72 | 21.54 ± 0.97 | 23.54 ± 1.03 | 25.34 ± 0.87 |
| Comparative example 6 | 4 | 19.94 ± 0.64 | 20.11 ± 1.05 | 21.12 ± 0.78 | 23.61 ± 0.78 | 26.07 ± 1.24 |
| Comparative example7 | 4 | 19.23 ± 0.53 | 20.64 ± 1.31 | 20.82 ± 1.24 | 22.34 ± 1.19 | 24.52 ± 1.23 |
| Comparative example 8 | 4 | 20.61 ± 0.86 | 21.31 ± 1.15 | 21.85 ± 1.17 | 23.94 ± 1.24 | 25.49 ± 1.07 |

| Groups | Day 35 | Day 42 | Day 49 | Day 56 |
|---|---|---|---|---|
| Blank group | 25.40 ± 1.12 | 26.49 ± 1.15 | 26.74 ± 0.79 | 27.85 ± 1.17 |
| Model group | 27.54 ± 0.97 | 28.70 ± 1.03 | 29.51 ± 1.06 | 29.95 ± 1.24 |
| Example 1 | 27.31 ± 1.12 | 27.01 ± 1.14 | 26.73 ± 1.02 | 26.47 ± 1.05 |
| Example 2 | 27.03 ± 1.01 | 27.62 ± 0.94 | 26.57 ± 1.24 | 26.24 ± 0.85 |
| Example 5 | 26.53 ± 1.00 | 27.08 ± 1.06 | 27.12 ± 1.24 | 26.21 ± 1.25 |
| Example 6 | 27.18 ± 1.32 | 27.31 ± 1.24 | 26.50 ± 1.26 | 26.37 ± 1.13 |
| Example 9 | 26.54 ± 0.97 | 27.12 ± 0.98 | 26.12 ± 0.94 | 26.04 ± 0.85 |
| Example 11 | 27.12 ± 0.78 | 27.48 ± 1.19 | 27.03 ± 1.13 | 26.56 ± 1.02 |
| Comparative example1 | 27.95 ± 1.12 | 28.32 ± 1.07 | 27.54 ± 1.19 | 26.97 ± 1.35 |
| Comparative example2 | 27.78 ± 1.35 | 27.98 ± 1.05 | 27.12 ± 0.98 | 27.05 ± 1.15 |
| Comparative example 3 | 27.69 ± 0.93 | 27.72 ± 1.07 | 27.77 ± 1.15 | 27.16 ± 1.35 |
| Comparative example 4 | 27.78 ± 1.26 | 27.84 ± 1.05 | 26.78 ± 1.35 | 27.62 ± 1.33 |
| Comparative example 5 | 27.54 ± 0.97 | 27.41 ± 1.27 | 27.54 ± 1.24 | 26.77 ± 1.01 |
| Comparative example 6 | 27.62 ± 0.67 | 27.46 ± 0.92 | 27.12 ± 1.18 | 27.25 ± 1.08 |
| Comparative example7 | 27.05 ± 0.78 | 27.06 ± 1.20 | 26.76 ± 1.01 | 26.54 ± 1.26 |
| Comparative example 8 | 27.59 ± 1.08 | 27.97 ± 1.26 | 27.75 ± 1.27 | 26.91 ± 1.37 |

PS: compare with the model group,
*P < 0.05 b) Effects of the Medicine of Each Group on the Serum TC, TG of the Mice with Hyperlipidemia After 3 weeks of administration, serum total cholesterol (TC) and triglyceride (TG) of the mice of each group were measured. The results can be seen in Table 4.

TABLE 4

Effects of the Chinese medicinal compositions of the present invention on the lipid of the mice ($\bar{X} \pm S$, n = 10)

| Group | Dose (g/kg) | TC (mmol/L) | TG (mmol/L) |
|---|---|---|---|
| Blank group | | 2.57 ± 0.29** | 1.25 ± 0.52** |
| Model group | | 5.84 ± 1.11 | 3.05 ± 0.44 |
| Example 1 | 4 | 3.11 ± 0.29** | 2.12 ± 0.50** |
| Example 2 | 4 | 3.28 ± 0.61** | 2.01 ± 0.36** |
| Example 5 | 4 | 3.09 ± 0.37** | 2.17 ± 0.41** |
| Example 6 | 4 | 3.36 ± 0.53** | 2.17 ± 0.30** |
| Example 9 | 4 | 2.98 ± 0.45** | 1.92 ± 0.27** |
| Example 11 | 4 | 3.24 ± 0.31** | 2.21 ± 0.48** |
| Comparative example 1 | 4 | 4.28 ± 0.34* | 2.61 ± 0.17* |
| Comparative example 2 | 4 | 3.38 ± 0.67** | 2.41 ± 0.27* |
| Comparative example 3 | 4 | 4.45 ± 0.39* | 2.62 ± 0.51* |
| Comparative example 4 | 4 | 4.54 ± 0.22* | 2.48 ± 0.32* |
| Comparative example 5 | 4 | 4.79 ± 1.07* | 2.76 ± 0.42* |
| Comparative example 6 | 4 | 4.74 ± 0.35* | 2.78 ± 0.32* |

TABLE 4-continued

Effects of the Chinese medicinal compositions of the present invention on the lipid of the mice ($\bar{X} \pm S$, n = 10)

| Group | Dose (g/kg) | TC (mmol/L) | TG (mmol/L) |
|---|---|---|---|
| Comparative example 7 | 4 | 3.65 ± 0.81** | 2.54 ± 0.46* |
| Comparative example 8 | 4 | 4.59 ± 0.46* | 2.67 ± 0.38* |

PS: compare with the model group,
*P < 0.05;
**P < 0.01

From table 4, it can be seen that the TC and TG level of the high lipid model were all significantly increased compared with the normal control group, indicating that the high lipid model of mice was successfully created. Compared with the model group, the group of the Chinese medicinal compositions of the present invention and the group of the comparative examples can significantly decrease the TC and TG level of mice, and the effects of the Chinese medicinal compositions of the present invention were better than that of the comparative examples, indicating that the effects of decreasing lipid of the compositions of the present invention were better than that of the comparative examples.

Summary: hyperlipidemia refers to elevated levels of cholesterol or triglyceride in plasma.

Hyperlipidemia is mainly related to cholesterol, the increase of cholesterol is one of the most important risks that cause the increase of mortality of cardiovascular and cerebrovascular diseases such as coronary heart disease. Dyslipidemia, especially the increase of the concentration of cholesterol, would easily lead to "condensed blood", and may cause deposition on the vessel wall, and gradually form small plaques (that is what we often called "atherosclerosis"), the number and size of these "plaques" increase, gradually clogging the blood vessels, cause the blood to flow more slowly, blood flow can even be interrupted when the situation getting serious; if this situation occurs in the heart, it causes coronary heart disease; if it occurs in the brain, it causes cardiovascular and cerebrovascular diseases such as stroke. Compared with the model group, the Chinese medicinal compositions of the present invention are very different in the decreasing of serum TC and TG of hyperlipidemia mice (**P<0.01), which show that the Chinese medicinal compositions of the present invention have a better effect than the Chinese medicinal compositions in the comparative examples in treating and preventing cardiovascular and cerebrovascular diseases.

Test Example 3

The Experiment of Reducing Blood Glucose

Experimental Material

Kunming mice, weight 18~22 g, male, provided by Vital River Animal Experiment Center.

Chinese medicinal compositions of the present invention and Chinese medicinal compositions of the comparative examples (self-made, the mixture of the corresponding extracts were prepared according to the methods of the examples and comparative examples of the present invention), were prepared to 0.2 g/mL with distilled water during the experiment (calculated based on the original dose of the composition).

Reagents: alloxan, insulin radioimmunoassay kit.

Instrument: glucose/blood ketone instrument and matched test papers, electric-heated thermostatic water bath, electronic balance, low-speed refrigerated centrifuge, radioimmunoassay counter.

Experiment Method

Preparation of Diabetic Model Mice:

Male mice were fed adaptively for one week. 10 were randomly selected as normal control, and the remaining mice were fasted (water was not inhibited) for 24 hours, 2% fresh solution was prepared by alloxan and saline, and was given through intraperitoneal injection in a dose of 200 mg/kg, after 72 hours, the tails were cut to collect blood and test blood glucose, the mice with 11.1 mmol/L blood glucose are diabetic model mice, and were involved in the experiment.

b) Grouping and Administration:

The diabetic model mice were randomly divided into groups, 10 for each group. The blood glucose of the groups were close, wherein one group was the model control group, 6 groups were the groups of the compositions of the present invention, 8 groups were the groups of the comparative examples. The mice of the groups received gavages of the corresponding medicine (the doses were the same as that of Test example 2), the corresponding amount of saline was given to the normal control group and the model control group, the weights were regularly weighed to adjust the amount of medicines that were given, lasted for 21 days.

c) Indicator Detection:

During the experiment, tails were cut on 0 day, 7 days, 14 days, 21 days to collect blood and detect blood glucose. Oral glucose tolerance test was carried out after the end of the gavage and the detect of blood glucose, the mice were given glucose through perfusion at a dose of 2.5 g/kg and were detected the blood glucose at 0 min, 30 min, 60 min, 120 min. At day 22, the blood was taken from the orbital of the mice, the serum was separated at 4° C., centrifuged for 10 min under 3000 rpm, the level of serum insulin was measured according to the instruction of the kits.

Experimental data were analyzed statistically using SPSS software, the results of the indicators were expressed in mean±standard deviation, the comparison between two groups were carried out by t test.

Results a) Effects on the Blood Glucose of the Alloxan Hyperglycemia Model Mice

After alloxan injection, blood glucose of the mice was significantly increased, the blood glucose of the mice that was administered for 7 days and 14 days were high, and were very different from the normal group, indicating that the alloxan induced diabetes model was successfully created, and the blood glucose of them were kept high during the experiment. 7 days after the administration, the blood glucose of the mice that were administered began to decrease, after 14 days of administration, the blood glucose of the mice of the group of the compositions of the present invention decrease significantly, compared with the model group, the differences were significant. After 21 days of gavages, the groups of the compositions of the present invention were significantly different (P<0.01), the groups of comparative examples were significantly different (P<0.05). The results showed that the compositions of the present invention had better effects on decreasing blood glucose, and the effects of decreasing blood glucose of the compositions of the present invention are better than the group of comparative examples. Oral glucose tolerance test showed that the Chinese medicinal compositions of the present invention largely improved the tolerance of the experimental mice to glucose (P<0.01), the groups of comparative examples can significantly improve the tolerance of the experimental mice to glucose (P<0.05). Results suggest that the effects of decreasing blood glucose of the Chinese medicinal compositions of the present invention are better than that of the comparative groups. See table 5.

TABLE 5

Effects of the Chinese medicinal compositions of the present invention on the blood glucose of the alloxan hyperglycemia model mice ($\bar{X} \pm S$, n = 10)

| Groups | Dose (g/kg) | Blood glucose (mmol/L) | | | |
|---|---|---|---|---|---|
| | | 0 h | 30 min | 1 h | 2 h |
| Blank group | | 6.57 ± 1.27** | 15.21 ± 3.42** | 13.40 ± 3.14** | 10.49 ± 2.57** |
| Model group | | 24.12 ± 3.49 | 26.27 ± 3.41 | 24.01 ± 4.12 | 22.43 ± 3.41 |
| Example 1 | 4 | 13.94 ± 2.56** | 18.64 ± 3.14** | 16.41 ± 2.08** | 15.42 ± 2.48** |
| Example 2 | 4 | 13.47 ± 2.14** | 17.51 ± 2.08** | 15.75 ± 3.77** | 14.81 ± 2.65** |
| Example 5 | 4 | 14.18 ± 3.27** | 19.21 ± 3.61** | 17.78 ± 2.24** | 14.97 ± 2.87** |
| Example 6 | 4 | 14.24 ± 2.31** | 19.74 ± 2.04** | 17.23 ± 2.02** | 16.42 ± 3.18** |
| Example 9 | 4 | 13.26 ± 2.45** | 17.11 ± 2.98** | 15.23 ± 3.41** | 13.85 ± 2.77** |
| Example 11 | 4 | 15.18 ± 3.12** | 18.61 ± 3.27** | 16.78 ± 3.24** | 15.87 ± 1.54** |
| Comparative example 1 | 4 | 19.24 ± 175* | 22.14 ± 2.71* | 20.37 ± 3.75* | 19.54 ± 3.20* |
| Comparative example 2 | 4 | 16.31 ± 3.21* | 20.71 ± 3.17* | 19.12 ± 2.74* | 17.71 ± 2.14* |
| Comparative example 3 | 4 | 19.84 ± 3.44* | 23.14 ± 2.47* | 21.37 ± 3.75* | 19.54 ± 3.14* |
| Comparative example 4 | 4 | 19.36 ± 2.37* | 22.71 ± 3.11* | 20.31 ± 2.62* | 18.71 ± 2.14* |
| Comparative example 5 | 4 | 18.98 ± 3.41* | 22.98 ± 1.52* | 20.77 ± 3.97* | 19.17 ± 3.27* |
| Comparative example 6 | 4 | 20.64 ± 2.15* | 23.74 ± 2.13* | 21.77 ± 3.07* | 19.52 ± 3.38* |
| Comparative example 7 | 4 | 17.11 ± 2.68* | 21.62 ± 1.62* | 19.54 ± 1.78* | 18.54 ± 2.64* |
| Comparative example 8 | 4 | 19.74 ± 3.36* | 21.47 ± 2.02* | 20.64 ± 2.74* | 18.95 ± 2.17* |

PS: compared with the model group,
*P < 0.05;
**P < 0.01 b) Effects on the Serum Insulin of the Alloxan Diapetic Model Mice

Compared with the normal pairs, the serum insulin level of the model mice was significantly reduced, indicating that after the intraperitoneal injection of alloxan, the function of the β cells of the mice were damaged, which means the models were successful created; compared with the model group, the serum insulin levels of the group of the Chinese medicinal compositions of the present invention and the group of comparative examples were increased at various degrees, wherein the groups of the Chinese medicinal compositions of the present invention had very significant differences (P<0.01), while the groups of comparative example 1, 2, 4, 7, 8 had significant differences (P<0.05), for the other groups of comparative examples, the serum insulin were increased, but there's no statistical significance, suggested that the effects of the compositions of the present invention on the increase of serum insulin of the alloxan diabetic mice were better than that of the group of comparative examples. The results can be seen in Table 6.

TABLE 6

Effects of the Chinese medicinal compositions of the present invention on the serum insulin of the alloxan diabetic mice ($\bar{X} \pm S$, n = 10)

| Groups | Dose (g/kg) | Serum insulin (μIU/mL) |
|---|---|---|
| Blank group | | 19.07 ± 2.67** |
| Model group | | 10.14 ± 2.49 |
| Example 1 | 4 | 16.14 ± 3.32** |
| Example 2 | 4 | 15.48 ± 3.04** |
| Example 5 | 4 | 16.58 ± 2.67** |
| Example 6 | 4 | 15.67 ± 3.12** |
| Example 9 | 4 | 17.08 ± 2.14** |
| Example 11 | 4 | 16.58 ± 2.27** |
| Comparative example 1 | 4 | 13.21 ± 2.41* |
| Comparative example 2 | 4 | 14.57 ± 1.35* |
| Comparative example 3 | 4 | 12.41 ± 2.47 |
| Comparative example 4 | 4 | 13.27 ± 1.45* |
| Comparative example 5 | 4 | 11.58 ± 1.67 |
| Comparative example 6 | 4 | 12.34 ± 1.14 |
| Comparative example 7 | 4 | 14.97 ± 1.86* |
| Comparative example 8 | 4 | 14.18 ± 2.15* |

PS: compare with the model group,
*P < 0.05,
**P < 0.01

Summary: With the improvement of people's living standards and the impact of environmental factors, abnormal glucose metabolism appeared more and more in patients with cardiovascular and cerebrovascular diseases, if patients with cardiovascular and cerebrovascular diseases have abnormal glucose metabolism at the same time, they may have poor prognosis. The risks of recurrent of myocardial infarction for diabetics that are once suffered from myocardial infarction are beyond 40%. In addition, the abnormal glucose level can cause pathological process such as endothelial dysfunction, the decrease of aortic elasticity, left ventricular hypertrophy, carotid atherosclerotic plaques, micro albuminuria, and ultimately lead to atherosclerosis. The Chinese medicinal compositions of the present invention can significantly decrease the blood glucose of the alloxan hyperglycemia model mice blood, improve the serum insulin of the alloxan diabetic mice, indicating that the Chinese medicinal compositions of the present invention have a good effect on treating and preventing cardiovascular and cerebrovascular diseases.

Test Example 4

Antithrombotic Experiment

1. Experimental Materials

SD rats, weight 180.0~220.0 g, male and female, provided by Vital River Animal Experiment Center, the rats were fed adaptively for a week in the animal room (the temperature was controlled) before the animal experiment.

Chinese medicinal compositions of the present invention and Chinese medicinal compositions of the comparative examples (self-made, the mixture of the corresponding extracts were prepared according to the methods of the examples and comparative examples of the present invention), were prepared to 0.15 g/mL with distilled water during the experiment (calculated based on the original dose of the composition).

Aspirin: white tablets, 50 mg/piece, provided by China Pharmaceutical Company Shanghai Branch. Pentobarbital sodium: white powder, provided by China Pharmaceutical (Group) Shanghai Chemical Reagent Company, was formulated to 0.8% water solution with saline for standby use. Heparin: white powder, 125 u/mg, China Pharmaceutical (Group) Shanghai Chemical Reagent Company, was formulated to 0.1% solution with saline for standby use. Sodium citrate: China Pharmaceutical Industry companies, Southwest Pharmaceutical factory one provided, was formulated to 3.8% solution with saline. ADP: produced by Sigma company, phosphate buffer with pH 7.4 was formulated to 200 µmol/L solution for standby use.

MK4/HC platelet counting instrument (USA Baker Instru-ments produced), Labor aggregometer-153 dual channel platelet aggregometer (German Labor GmbHHanburg Company)

2. Experiment Method

The rats were randomly divided into groups, each group was composed of 15 rats, that is, the blank control group, aspirin group (1% CMC-Na solution, grinded, and was formulated to 0.88 mg/mL suspension, according to 0.0044 g/kg/d), the groups of the Chinese medicinal compositions of the present invention (6 groups, the doses were the same as that in test example 1), the groups of comparative examples (8 groups, the doses were the same as that in test example 1). The same volume of saline was given to the Blank control group. The rats were administered once a day for 7 days.

Experiments of thrombus formation, in vivo: 1 h after 7 days of administration, the rats of the groups were hypnotized through intraperitoneal injection with 0.8% sodium pentobarbital, with a dose of 40 mg/kg referring to the artery-vein shunt thrombosis method [Zhang Jun Tian. Modern pharmacology experimental methods. Beijing: Beijing Medical University Press, 1998; 1216-1217], right common carotid artery and left external jugular vein were separated. Three sections of polyethylene plastic pipe were taken, the diameter of the middle section was 2 mm, the length was about 8.5 cm, the diameter of the two plastic pipe of the two ends were 1.5 mm, the length were 10 cm respectively. A No 4 operation silk thread that was weighed previously with a length of about 7 cm was placed in the plastic pipe in the middle section, wherein one end of the thread with the length of 0.5 cm was exposed to the pipe to fix the position, and a silk thread with a length of 6.5 cm was kept in the pipe, the polyethylene plastic pipe was filled with heparin solution, one end of the plastic tube was inserted into the left external jugular vein, the other end of the plastic tube was inserted into the right common carotid artery, then the bloodstream was opened immediately. 20 minutes after the bloodstream was opened, the blood flow was interrupted immediately and the silk thread in the middle section was quickly taken out, the silk was weighed and the weight was regarded as the total weight. The total weight minus the weight of the thread was the wet weight of thrombus. The thrombosis inhibition rate was calculated according to the following formula:

Inhibition rate=(wet weight of thrombus in the control group−wet weight of thrombus in the control group in the experimental group)/wet weight of thrombus in the control group×100%. The wet weight of thrombus in each group were compared statistically.

Platelet aggregation inhibition test: 1 h after 7 days of administration to the rats of the groups, the rats were hypnotized according to the above method, a tube was inserted into the common carotid artery to collect blood, the blood was added 3.8% sodium citrate in a ratio of 1:9 to become anticoagulant, when it was centrifuged for 5 minutes at 500 rpm, the upper portion of the plasma was taken to be the platelet-rich plasma (PRP), the remaining part was centrifuged again for 15 minutes at 3,500 rpm, the supernatant was platelet poor plasma (the PPP), the number of platelet of PRP was counted with platelet counting instrument, the number of platelet of PRP was adjusted with PPP to about $3 \times 10^5/mm^2$. The temperature of the sample tube was kept at 37° C. for 3 minutes, then 5 µL ADP was added (final concentration 5 µmol/L), stirring speed of the stirrer was 500 r/min, the space between the rows of the movement of the recording pen was recorded after adding, and the aggregation rate was calculated according to the following formula:

Aggregation rate(%)=the itinerary of adding ADP× 100%/0~100% of the itinerary

The average accumulation rates and the standard deviations of each experimental group were calculated, and the platelet aggregation inhibition rates for each experimental group were calculated according to the following formula:

Aggregation inhibition rate(%)=(aggregation rate of the control group−aggregation rate of the experimental group)/aggregation rate of the control group×100%.

3. Results a) Effect on the Experimental Thrombosis

Compared with the blank control group, in the groups that received medicines, there were significant inhibiting effects on the thrombosis, compared with the control group, the wet weights of the thrombuses of rats of the groups of the Chinese medicinal composition of the present invention, the groups of the Chinese medicinal compositions of comparative example 2 and example 7 were significantly different (P<0.01), the wet weights of the thrombus of rats of the groups of the Chinese medicinal compositions of comparative example 1, comparative example 3, comparative example 4, comparative example 5, comparative example 6 and comparative example 8 (P<0.05) were significantly different (P<0.05), indicating that the effects on thrombosis of rats of the Chinese medicinal composition of the present invention were better than that of the comparative group. The results can be seen in table 7.

TABLE 7

Effect of the Chinese medicinal compositions of the present invention on thrombosis of rats ($\overline{X} \pm S$, n = 15)

| Groups | Doses (g/kg) | Wet weights of thrombus/g | Inhibition rate/% |
|---|---|---|---|
| Control group | — | 0.081 ± 0.018 | / |
| Aspirin group | 0.0044 | 0.056 ± 0.011* | 30.86 |
| Example 1 | 3 | 0.040 ± 0.002** | 50.62 |
| Example 2 | 3 | 0.041 ± 0.004** | 49.38 |
| Example 5 | 3 | 0.036 ± 0.005** | 55.56 |
| Example 6 | 3 | 0.042 ± 0.004** | 48.15 |
| Example 9 | 3 | 0.035 ± 0.004** | 56.79 |
| Example 11 | 3 | 0.038 ± 0.006** | 53.09 |
| Comparative example 1 | 3 | 0.050 ± 0.004* | 38.27 |
| Comparative example 2 | 3 | 0.045 ± 0.005** | 44.44 |
| Comparative example 3 | 3 | 0.054 ± 0.009* | 33.33 |
| Comparative example 4 | 3 | 0.049 ± 0.003* | 39.51 |
| Comparative example 5 | 3 | 0.058 ± 0.005* | 28.40 |
| Comparative example 6 | 3 | 0.055 ± 0.007* | 32.10 |
| Comparative example 7 | 3 | 0.046 ± 0.005** | 43.21 |
| Comparative example 8 | 3 | 0.052 ± 0.005* | 35.80 |

PS: compared with the control group,
*P < 0.05;
**P < 0.01

(2) Effect on Platelet Aggregation

During the experiment, the number of platelet of the blood samples collected from the groups of animals was about $3 \times 10^5/mm^2$, there's no significant difference. The results can be seen in table 8.

TABLE 8

Effect of the Chinese medicinal compositions of the present invention on platelet aggregation of rats ($\overline{X} \pm S$, n = 15)

| Groups | Doses (g/kg) | Platelet aggregation % | aggregation inhibition rate/% |
|---|---|---|---|
| Control group | — | 46.14 ± 5.23 | / |
| Aspirin group | 0.0044 | 23.27 ± 3.06* | 49.57 |
| Example 1 | 3 | 16.27 ± 3.17** | 64.74 |
| Example 2 | 3 | 17.51 ± 2.32** | 62.05 |
| Example 5 | 3 | 14.17 ± 5.28** | 69.29 |
| Example 6 | 3 | 17.27 ± 3.27** | 62.57 |
| Example 9 | 3 | 13.51 ± 2.32** | 70.72 |
| Example 11 | 3 | 15.67 ± 4.58** | 66.04 |
| Comparative example 1 | 3 | 27.15 ± 4.12* | 41.16 |
| Comparative example 2 | 3 | 19.14 ± 3.21* | 58.52 |
| Comparative example 3 | 3 | 22.96 ± 4.31* | 50.24 |
| Comparative example 4 | 3 | 24.14 ± 5.72* | 47.68 |
| Comparative example 5 | 3 | 26.21 ± 3.53* | 43.19 |
| Comparative example 6 | 3 | 29.45 ± 4.32* | 36.17 |
| Comparative example 7 | 3 | 20.87 ± 3.54* | 54.77 |
| Comparative example 8 | 3 | 27.67 ± 4.31* | 40.03 |

PS: compared with the control group,
*P < 0.05;
**P < 0.01

From the above table, it can be seen that compared with the blank control group, in the groups that receive medicines, there were inhibitions to the ADP induced platelet aggregation of rats. The aggregation inhibition rates of the Chinese medicinal compositions of the present invention (compared with the control group, **P<0.01) were beyond that of the groups of comparative examples (compared with the control group, *P<0.05), indicating that the effects on anti-platelet aggregation of the Chinese medicinal compositions of the present invention were better than that of the comparative groups.

Summary: Thrombus is an aggregation of some of the ingredients in the blood to form clumps, which affects blood flow. The reasons of the appearance of thrombus are mainly the change of the components of the blood, vascular endothelial damage and changes in blood flow velocity. Thrombus can block the coronary blood vessels, resulting in a sharp reduction or interruption of blood flow, causing severe and persistent acute ischemia of the corresponding cardiac muscles, resulting in ischemic myocardial necrosis; in addition, certain parts of the brain blood vessels spontaneous thrombosis, resulting in the block of brain blood vessels, poor blood circulation, the formation of "cerebral thrombus", after cerebral thrombosis, thrombosis shed off then cause the block of blood vessels, and thus result in cerebral infarction. Compared with the Chinese medicinal compositions of the comparative examples, the Chinese medicinal compositions of the present invention have better effect on reducing the size of thrombus, inhibiting thrombosis and reducing the aggregation of platelet, suggesting that the Chinese medicinal compositions of the present invention have better effects on the treatment and prevention of cardiovascular and cerebrovascular diseases.

Test Example 5

Effects on Scopolamine Hydrobromide Induced Acquired Memory Disorder Model Mice

1. Experimental Materials

ICR mice, 18-22 g, half male and half female, provided by Beijing Vital River Laboratory Animal Technology Development Company Ltd.

Chinese medicinal compositions of the present invention and Chinese medicinal compositions of the comparative examples (self-made, the mixture of the corresponding extracts were prepared according to the methods of the examples and comparative examples of the present invention), were prepared to 0.2 g/mL with distilled water during the experiment (calculated based on the original dose of the composition).

Huperzine (huperzine A tablets), 50 µg/piece, produced by Henan Zhu Lin Zhong Sheng Pharmaceutical Co., Ltd., and was formulated to 4 µg/mL with distilled water during the experiment; tanakan tablets (tanakan), standardized Ginkgo leaf extract (Egb761) 40 mg/tablet, produced by France Beaufort-Ipsen pharmaceutical industry Co., Ltd., and was formulated to 1.5 mg/mL with distilled water during the experiment; scopolamine hydrobromide, 0.6 mg/mL, Shanghai Hefeng pharmaceutical Co.

TT-2 type mice jumping program automatic controller: produced by Institute of pharmacology, Chinese Academy of Medical Sciences.

2. Experiment Method

Half male animals and half female animals, the animals were randomly divided into groups: blank control group, model group, Huperzine 0.08 mg/kg group, tanakan 30 mg/kg group, the groups of the Chinese medicinal compositions of the present invention (6 groups, the doses were the same as that of test example 2), the groups of comparative examples (8 groups, the doses were the same as that of test example 2).

The animals were intragastric administered once a day at a dose of 20 mL/kg, distilled water was given to blank control group and model group, one time a day, lasted for 15 days, 50 minutes after the administration on the 14$^{th}$ day, saline was given to the mice of blank control group through intraperitoneal injection in a volume of 10 ml/kg, the rest animals were given scopolamine through injection (6 mg/kg). 10 minutes later, the mice were placed on the jumping program automatic controller, to adapt for 3 minutes, then power on, the mice were stimulated by electric shock for 5 times, when the mice were stimulated, they jump to the diving platform to avoid electric shock, trained 5 minutes to obtain memory. 60 minutes after the administration on the 15$^{th}$ day, the animals were placed on the jumping program automatic controller, the number of times that the mice left the jump platform and received electric shock and the time of occurrence (the incubation period) were determined (number of errors). The results were analyzed statistically (t test). See table 9.

TABLE 9

Effects of the compositions of the present invention on scopolamine hydrobromide induced acquired memory disorder rats ($\overline{X} \pm S$, n = 12)

| Groups | Doses (g/kg) | Within 5 minutes | |
|---|---|---|---|
| | | number of errors | the incubation period (s) |
| Blank group | | 0.3 ± 0.7* | 292.2 ± 31.4** |
| Model group | | 1.9 ± 1.4 | 206.7 ± 53.4 |
| Huperzine group | 0.00008 | 0.6 ± 0.6* | 281.6 ± 39.4** |
| Tanakan group | 0.03 | 0.7 ± 0.4* | 237.5 ± 82.8* |
| Example 1 | 4 | 0.5 ± 0.6* | 268.6 ± 73.1** |
| Example 2 | 4 | 0.7 ± 0.4* | 277.5 ± 62.8** |
| Example 5 | 4 | 0.8 ± 0.7* | 279.2 ± 93.1** |
| Example 6 | 4 | 0.6 ± 0.5* | 274.4 ± 72.0** |
| Example 9 | 4 | 0.6 ± 0.5* | 283.1 ± 52.8** |
| Example 11 | 4 | 0.8 ± 0.7* | 280.6 ± 43.2** |
| Comparative example 1 | 4 | 1.1 ± 0.7* | 232.1 ± 42.7* |
| Comparative example 2 | 4 | 0.9 ± 0.7* | 252.7 ± 33.7* |
| Comparative example 3 | 4 | 1.0 ± 0.4* | 236.4 ± 52.4* |
| Comparative example 4 | 4 | 1.1 ± 0.7* | 246.7 ± 63.1* |
| Comparative example 5 | 4 | 1.4 ± 0.6 | 228.9 ± 51.2* |
| Comparative example 6 | 4 | 1.5 ± 1.1 | 223.4 ± 42.3* |
| Comparative example 7 | 4 | 1.0 ± 0.3* | 241.7 ± 56.9* |
| Comparative example 7 | 4 | 1.0 ± 0.6* | 231.7 ± 32.2* |

PS: compare with the model group,
*P < 0.05;
**P < 0.01

Results: compared with the model group, the number of errors of the mice of the blank control group within 5 minutes were significantly decreased (P<0.05), the incubation period was prolonged significantly (P<0.01), indicating that the models were created successfully. Compared with the model group, the number of errors of the mice of the huperzine group within 5 minutes were significantly decreased (P<0.05), the incubation period was prolonged significantly (P<0.01); the number of errors of the mice of the groups of the Chinese medicinal compositions of the present invention within 5 minutes were significantly decreased (P<0.05), the incubation periods were prolonged significantly (P<0.01); the number of errors of the mice of the tanakan group and the groups of the Chinese medicinal compositions of comparative examples 1-4, 7, 8 within 5 minutes were significantly decreased (P<0.05), the incubation periods were prolonged significantly (P<0.01). The number of errors of the groups of Chinese medicinal compositions of comparative examples 5, 6 have tendencies to decrease, the incubation periods thereof have tendencies to extend, there's no statistical significance.

Summary: The mice were given M-receptor antagonist scopolamine before training, which can cause the decrease of the content of acetylcholine in the brain, causing acquired memory impairment. In this experiment, the platform test is carried out based on this chemical injury, the number of errors of mice in 5 minutes and the incubation periods were regarded as the indicators, the effects of the compositions of the present invention and the compositions of the comparative examples on the model were observed. The results showed that the Chinese medicinal compositions of the present invention significantly improve the scopolamine induced acquired memory disorders of the mice, the effects are better than that of the comparative groups, suggesting that the Chinese medicinal compositions of the present invention may have effects of increasing the content of acetylcholine in the brain, and the effects are stronger than that of the comparative groups.

Test Example 6

Effects on Reserpine Induced Acquired Memory Disorder Model Mice

1. Experimental Materials

ICR mice, 25-32 g, half male and half female, provided by Beijing Vital River Laboratory Animal Technology Development Company Ltd.

Chinese medicinal compositions of the present invention and Chinese medicinal compositions of the comparative examples (self-made, the mixture of the corresponding extracts were prepared according to the methods of the examples and comparative examples of the present invention), were prepared to 0.2 g/mL with distilled water during the experiment (calculated based on the original dose of the composition).

Huperzine (huperzine A tablets), 50 μg/piece, produced by Henan Zhu Lin Zhong Sheng Pharmaceutical Co., Ltd., and was formulated to 4 μg/mL with distilled water during the experiment; tanakan tablets (tanakan), standardized Ginkgo leaf extract (Egb761) 40 mg/tablet, produced by France Beaufort-Ipsen pharmaceutical industry Co., Ltd., and was formulated to 1.5 mg/mL with distilled water during the experiment; reserpine injection, 1 mg/mL, Hong Qi pharmaceutical factory of Shanghai Medical University, and was formulated to 0.05 mg/mL with distilled water during the experiment.

TT-2 type mice jumping program automatic controller: produced by Institute of pharmacology, Chinese Academy of Medical Sciences.

2. Experiment Method

Experimental grouping was the same as that of test example 5.

The animals were intragastric administered once a day at a dose of 20 mL/kg, distilled water was given to the blank control group and the model group, one time a day, lasted for 15 days. After the administration on the $14^{th}$ day, saline was given immediately to the mice of the blank control group through back and neck subcutaneous injection in a volume of 10 ml/kg, the rest animals were given reserpine hydrochloride (0.5 mg/kg) through back and neck subcutaneous injection. 60 minutes after the injection, the mice were placed on the jumping program automatic controller, to adapt for 3 minutes, then power on, the mice were stimulated by electric shock for 5 times, when the mice were stimulated, they jump to the diving platform to avoid electric shock, trained 5 minutes to obtain memory. 60 minutes after the administration on the $15^{th}$ day, the animals were placed on the jumping program automatic controller, the number of errors and the incubation period of mice within 5 minutes were determined. The results were analyzed statistically (t test).

3. Results

Compared with the model group, the number of errors of the mice of the blank control group within 5 minutes were significantly decreased (P<0.05), the incubation period was prolonged significantly (P<0.01), indicating that the model was created successfully. Compared with the model group, the number of errors of the mice of the group of the Chinese medicinal compositions of the present invention within 5 minutes were significantly decreased (P<0.05), the incubation period was prolonged significantly (P<0.05). the number of errors of the mice of the comparative medicine group, huperzine group and tanakan group within 5 minutes were significantly decreased (P<0.05), the incubation period have tendencies to extend, but there's no statistical significance. See table 10.

TABLE 10

Effects of the compositions of the present invention on reserpine induced acquired memory disorder mice ($\overline{X} \pm S$, n = 12)

| Groups | Doses (g/kg) | Within 5 min | |
|---|---|---|---|
| | | number of errors | the incubation period (s) |
| Blank group | | 0.5 ± 0.8* | 283.1 ± 35.6* |
| Model group | | 2.1 ± 1.7 | 186.7 ± 81.7 |
| Huperzine group | 0.00008 | 0.6 ± 0.9* | 243.1 ± 38.4 |
| Tanakan group | 0.03 | 0.5 ± 0.8* | 245.7 ± 87.9 |
| Example 1 | 4 | 0.3 ± 0.5* | 272.3 ± 63.7* |
| Example 2 | 4 | 0.5 ± 0.4* | 267.1 ± 72.1* |
| Example 5 | 4 | 0.4 ± 0.7** | 273.6 ± 63.5* |
| Example 6 | 4 | 0.6 ± 0.5* | 264.8 ± 57.9* |
| Example 9 | 4 | 0.6 ± 0.5* | 275.3 ± 62.6* |
| Example 11 | 4 | 0.3 ± 0.7* | 280.4 ± 75.3* |
| Comparative example 1 | 4 | 1.1 ± 0.5* | 221.7 ± 37.2 |
| Comparative example 2 | 4 | 0.7 ± 0.6* | 243.5 ± 61.5 |
| Comparative example 3 | 4 | 0.9 ± 0.7* | 206.8 ± 72.3 |
| Comparative example 4 | 4 | 1.0 ± 0.6* | 238.1 ± 55.4 |
| Comparative example 5 | 4 | 1.5 ± 0.9 | 217.2 ± 43.7 |
| Comparative example 6 | 4 | 1.6 ± 1.1 | 228.4 ± 52.6 |
| Comparative example 7 | 4 | 0.8 ± 0.5* | 248.4 ± 47.5 |
| Comparative example 8 | 4 | 1.2 ± 1.1 | 209.4 ± 85.1 |

PS: compared with the model group,
P < 0.05;
**P < 0.01

Summary: The study confirmed that reserpine can cause the depletion of monoamine neurotransmitter in brain, damage to learning and memory process, giving the mice reserpine before the training can cause them to obtain or retain memory impairment. The number of errors and the incubation time when the errors happened within 5 minutes were determined to be the indicator of the present experiment, the effects of the Chinese medicinal compositions of the present invention and the groups of the comparative examples on the model were observed. After the mice were given gavages of the Chinese medicinal compositions of the present invention and the compositions of the comparative examples, the two indicators received improvements of different degrees, and the improvements of the groups of the Chinese medicinal compositions of the present invention are much better than that of the group of comparative examples, indicating that the Chinese medicinal compositions of the present invention have effects of improving the acquired memory impairment of animals, suggesting that it is related to the mechanism that the Chinese medicinal compositions of the present invention can increase the content of the catecholamine neurotransmitter, and effects of the Chinese medicinal compositions of the present invention are better than that of the comparative examples.

Test Example 7

Effects on Sodium Nitrite Induced Acquired Consolidate Memory Disorder Model Mice 1. Experimental Materials ICR mice, 18-22 g, half male and half female, provided by Beijing Vital River Laboratory Animal Technology Development Company Ltd.

Chinese medicinal compositions of the present invention and Chinese medicinal compositions of the comparative examples (self-made, the mixture of the corresponding extracts were prepared according to the methods of the examples and comparative examples of the present invention), were prepared to 0.2 g/mL with distilled water during the experiment (calculated based on the original dose of the composition).

Huperzine (huperzine A tablets), 50 μg/piece, produced by Henan Zhu Lin Zhong Sheng Pharmaceutical Co., Ltd., and was formulated to 4 μg/mL with distilled water during the experiment; tanakan tablets (tanakan), standardized Ginkgo leaf extract (Egb761) 40 mg/tablet, produced by France Beaufort-Ipsen pharmaceutical industry Co., Ltd., and was formulated to 1.5 mg/mL with distilled water during the experiment; sodium nitrite, produced by Beijing Yili fine chemicals Co., and was formulated to 12 mg/mL with saline during the experiment.

TT-2 type mice jumping program automatic controller: produced by Institute of pharmacology, Chinese Academy of Medical Sciences.

2. Experiment Method

Experimental grouping was the same as that of test example 5.

The animals were intragastric administered once a day at a dose of 20 mL/kg, distilled water was given to the animals of blank control group and model group, one time a day, lasted for 15 days. 60 minutes after the administration on the 14$^{th}$ day, the mice were placed on the jumping program automatic controller, to train for 5 minutes, and the mice were stimulated by electric shock for 5 times. After the treatment, saline was given immediately to the mice of comparative group through back and neck subcutaneous injection in a volume of 10 ml/kg, sodium nitrite (120 mg/kg) were injected to the rest of the animals. 60 minutes after the administration on the 15$^{th}$ day, the animals of the groups were placed on the jumping program automatic controller, the number of errors and the incubation period of mice within 5 minutes were determined. The results were analyzed statistically (t test).

3. Results

Compared with the model group, the number of errors of the mice of the blank control group within 5 minutes were significantly decreased (P<0.05), the incubation period was prolonged significantly (P<0.01), indicating that the models were created successfully. Compared with the model group, the number of errors of the mice of the group of the Chinese medicinal compositions of the present invention, the huperzine group and the tanakan group within 5 minutes were significantly decreased (P<0.05), the incubation period was prolonged significantly (P<0.01~0.05). The number of errors of the mice of the group of the Chinese medicinal composition of the comparative example 7 within 5 minutes were significantly decreased (P<0.05), the incubation period was significantly prolonged (P<0.05). The number of errors of the mice of the group of the Chinese medicinal composition of the comparative example 2 within 5 minutes were significantly decreased (P<0.05), the incubation period had the tendency to extend, but there's no statistical significance. The number of errors of the other comparative groups had tendencies to decrease, the incubation times had tendencies to extend, there's no statistical significance. The results can be seen in table 11.

TABLE 11

Effects of the composition of the present invention on sodium nitrite induced consolidate memory disorder mice ($\overline{X} \pm S$, n = 12)

| groups | doses (g/kg) | Within 5 min | |
|---|---|---|---|
| | | Number of errors | The incubation time (s) |
| Blank group | | 0.1 ± 0.3* | 295.2 ± 16.4** |
| Model group | | 1.2 ± 0.8 | 176.6 ± 94.7 |
| Huperzine group | 0.00008 | 0.5 ± 0.7* | 229.1 ± 94.6* |
| Tanakan group | 0.03 | 0.3 ± 0.6* | 290.3 ± 23.4** |
| Example 1 | 4 | 0.4 ± 0.7* | 267.9 ± 83.9* |
| Example 2 | 4 | 0.3 ± 0.7* | 260.1 ± 81.2* |
| Example 5 | 4 | 0.4 ± 0.7* | 287.1 ± 53.6** |
| Example 6 | 4 | 0.6 ± 0.9* | 279.6 ± 58.7** |
| Example 9 | 4 | 0.4 ± 0.6* | 288.4 ± 92.1** |
| Example 11 | 4 | 0.5 ± 0.8* | 274.5 ± 67.3* |
| Comparative example 1 | 4 | 0.9 ± 0.5 | 237.6 ± 28.9 |
| Comparative example 2 | 4 | 0.8 ± 0.4* | 241. ± 65.5 |
| Comparative example 3 | 4 | 0.9 ± 0.8 | 228.6 ± 71.7 |
| Comparative example 4 | 4 | 1.2 ± 0.8 | 236.3 ± 58.4 |
| Comparative example 5 | 4 | 1.1 ± 0.9 | 203.4 ± 67.7 |
| Comparative example 6 | 4 | 1.3 ± 1.0 | 214.5 ± 72.6 |
| Comparative example 7 | 4 | 0.8 ± 0.6* | 244.8 ± 51.4* |
| Comparative example 8 | 4 | 1.1 ± 0.8 | 211.5 ± 64.9 |

PS:
compared with the model group *P < 0.05; **P < 0.01

The study confirmed that sodium nitrite can cause the denaturation of hemoglobin, thus cause the ischemia and hypoxia of the brain tissue, damage the learning and studying process, giving the mice sodium nitrite immediately after training would cause the consolidate or retain impairment of memory of the mice. On the basis of this chemical damage, with the number of errors and the incubation time being the indicators in the present experiment, the effects of the compositions of the present invention and the compositions of the comparative examples on the models were observed. After the mice were given gavages of the compositions of the present invention and the compositions of the comparative examples, the two indicators received improvements of different degrees, and the improvements of the groups of the compositions of the present invention are much better than that of the group of comparative examples, indicating that the compositions of the present invention have effects of improving the consolidate memory impairment of animals, suggesting that the Chinese medicinal compositions of the present invention may improve the memory of studying by improving the circulation of the brain and improving the ischemia and hypoxia of the brain tissue, and the effects of the Chinese medicinal compositions of the present invention are better than that of the comparative examples.

Test Example 8

Effects on the VaD Caused by the Permanent Ligation of Bilateral Common Carotid Artery of Rats 1. Experimental Material (1) Animals: SD rats, weight 250-270 g, male. Provided by Beijing Vital River Laboratory Animal Technology Development Company Ltd.

(2) Medicines:

The Chinese medicinal compositions of the present invention and Chinese medicinal compositions of the comparative examples (self-made, the mixture of the corresponding extracts were prepared according to the methods of the examples and comparative examples of the present invention), were prepared to 0.3 g/mL with distilled water during the experiment (calculated based on the original dose of the composition).

Huperzine (huperzine A tablets), 50 μg/piece, produced by Henan Zhu Lin Zhong Sheng Pharmaceutical Co., Ltd., and was formulated to 6 μg/mL with distilled water during the experiment; tanakan tablets (tanakan), standardized Ginkgo leaf extract (Egb761) 40 mg/tablet, produced by France Beaufort-Ipsen pharmaceutical industry Co., Ltd., and was formulated to 2 mg/mL with distilled water during the experiment.

(3) Reagents:

High Performance Liquid: acetylcholine chloride (AchCl), disodium hydrogen phosphate ($Na_2HPO4$), chloride, tetramethyl ammonium chloride (TMACl), sodium octanesulfonate (OSA), sodium thiosulfate ($Na_2S_2O5$), ethylene diamine tetraacetic acid tetrasodium salt (EDTA), all HPLC grade, produced by Sigma, USA; phosphoric acid ($H_3PO_4$, 85%), perchloric acid ($HClO_4$), all are HPLC grade, produced by Fisher Scientific company, USA; MB reagent, produced by ESA company, USA.

Biochemical measurements: acetylcholinesterase (TCHE) kit; superoxide dismutase (SOD) kit; malondialdehyde (MDA) kit; protein quantitation (biuret method) kit; all provided by Jiancheng Institute of Bioengineering of Nanjing; neuropeptide Y (NPY) kit, provided by RIA center of Science and technology development center of PLA General Hospital; β-endorphin (β-EP) kit, provided by the Navy RIA technology center.

(4) Instrument:

MORRIS water maze, produced by Institute of Medicines of Chinese Academy of Medical Sciences. FT-630Gγ-counter, produced by Beijing nuclear plant. Spectrophotometer, UV-120-02, produced by Shimadzu company, Japan. 16 Channels Coularray Cullen array electrochemical high performance liquid chromatography and chromatography workstation, 582 pumps, 5600 A electrochemical detector, auto sampler 542, 5040 type solid porous electrode (platinum electrode, solid palladium electrodes), CH150 type column oven, immobilized enzyme reactor before columns, immobilized enzyme reactor after columns, the products are all from ESA company, USA; columns (C18150×3 mm I.D.), products of ESA company, USA; ultracentrifuge 55P-72, a product of HITACHI company, Japan; cryogenic refrigerators, products of JOUAN company, France; syringe microporous membrane filter: aqueous membrane (0.22 μm), product of Tianjin Tengda filter factory.

(5) Conditions for the determination of the content of acetylcholine (ACh)

Mobile phase: $Na_2HPO_4$ (100 mmol/L), TMACl (0.5 mmol/L), OSA (2.0 mmo/L), MB reagent (0.005% v/v), diluted with redistilled water, 85% PH was adjusted to 8.00 by $H_3PO_4$, filtered by 0.22 μm aqueous membrane.

Chromatographic conditions: ESA582 type binary pump system, ESA ACH-3 column (150×3 mm 5 μm I.D.), former ESA immobilized enzyme reactor before columns (ESA ACH-SPR, 3 cm), flow rate, 0.35 mL/min, column temperature, 35° C.

Test conditions: 5600 A electrochemical detector; 5040 type solid porous electrode (platinum working electrode, a solid state palladium reference electrode) potential: +300 mV.

2. Experiment Method

Sham group, model group, Huperzine group, tanakan group, the groups of the Chinese medicinal composition of the present invention (six groups, the doses were the same as that in test example 1), the groups of the comparative examples (8 groups, the doses were the same as that in test example 1).

Rats were anaesthetized with chloral hydrate (350 mg/kg), incisions were made in the middle of the necks, bilateral common carotid arteries were separated and received a ligation (the arteries were only separated but did not receive a ligation in the sham group), sutured the wounds of the rats then fed them in cages, the rats received an anti-infective process with penicillin for 4 days. One month later, a swimming test in the MORRIS water maze was carried out, the rats with a tendency of learning and memory impairment were selected with the time of duration being the indicator, the rats were randomly grouped: the model group; Huperzine 60 μg/kg group; tanakan 20 mg/kg group; the group of the Chinese medicinal compositions of the present invention and the group of the Chinese medicinal compositions of the comparative examples (the doses are the same as that of experimental example 1), the rats were intragastric administered once a day (10 mL/kg) for 2 months. The sham group and the model group were given gavages of distilled water of the same volume. 2 months, 3 months after the models were created (1 month and 2 months after the administration), the time of the duration of MORRIS water maze were measured. After the last measurement, blood was taken from abdomens aorta, the brain was taken quickly, and the left hemisphere was solidified with liquid nitrogen. In ice bath, with 0.15M $HCLO_4$ homogenates (1 ml was added for 100 mg brain weight) 14000×g 4° C., centrifuged for 20 min, the supernatant was taken, filtered with 0.22 μm membrane, 10 μl was fed into the auto sampler, the content of Ach was determined using HPLC; right hemisphere, 4 for each group, were solidified with formalin, dehydrated, embedded, sliced, HE dyed for pathological examination, homogenates of six brain tissue, AchE, SOD activity and MDA content (colorimetric method) were measured; Indicators such as neuropeptide Y, β-EP in plasma were determined (RIA). The results were analyzed statistically (t test).

3. Results 3.1 Effects on the Time of Duration in the Water Maze of Rats

After one month of the ligation of the bilateral common carotid arteries of rats, although the tendency of learning and memory impairment appeared, but compared with the sham group, there were not great differences. Two months, three months after the ligation, compared with the model group, for the time of duration in the MORRIS water maze of rats, the time of the sham group was significantly shorter than that of the model group (P<0.01), indicating that the models were created successfully. After 2 months to 3 months administration, the learning and memory ability of the rats of the Chinese medicinal composition of the present invention are all significantly improved, compared with the model group, the time of duration was significantly shortened (P<0.01); same effects were found in the comparative medicine Huperzine group and the group of the Chinese medicinal compositions of the comparative example 2, comparative example 3, comparative example 6 and comparative example 7 (P<0.05~0.01); 3 months after the administration, the learning and memory ability of the rats of the comparative medicine Tanakan group has a tendency of improving, there's no statistical significance. The results can be seen in table 12.

TABLE 12

Effects on the time of duration in MORRIS water maze of VaD rats ($\bar{X} \pm S$)

| groups | doses (g/kg) | n | time (s) 1 month after the model was created | 2 months after the model was created | 3 months after the model was created |
|---|---|---|---|---|---|
| Sham group | | 11 | 34.6 ± 32.7 | 9.2 ± 6.8** | 7.3 ± 4.2** |
| Model group | | 10 | 57.6 ± 21.4 | 54.9 ± 31.2 | 43.7 ± 29.6 |
| Huperzine group | 0.00006 | 10 | 58.6 ± 26.6 | 24.6 ± 19.0* | 9.0 ± 5.2** |
| Tanakan group | 0.02 | 10 | 57.1 ± 25.4 | 46.8 ± 38.7 | 21.8 ± 15.1 |
| Example 1 | 3 | 10 | 56.5 ± 23.6 | 18.3 ± 11.9** | 13.7 ± 8.9** |
| Example 2 | 3 | 10 | 54.7 ± 28.8 | 17.4 ± 15.8** | 14.4 ± 11.8** |
| Example 5 | 3 | 10 | 57.4 ± 18.6 | 22.2 ± 27.1** | 8.7 ± 7.1** |
| Example 6 | 3 | 10 | 55.1 ± 24.1 | 14.4 ± 12.0** | 9.4 ± 8.2** |
| Example 9 | 3 | 10 | 57.6 ± 12.5 | 13.1 ± 10.8** | 8.5 ± 4.8** |
| Example 11 | 3 | 10 | 54.8 ± 19.7 | 18.6 ± 13.2** | 10.2 ± 13.2** |
| Comparative example 1 | 3 | 10 | 57.1 ± 20.7 | 32.8 ± 12.7* | 22.5 ± 12.3 |
| Comparative example 2 | 3 | 10 | 56.8 ± 21.6 | 25.7 ± 13.5* | 18.9 ± 10.5* |
| Comparative example 3 | 3 | 10 | 57.1 ± 26.4 | 23.4 ± 15.4** | 17.4 ± 14.2** |
| Comparative example 4 | 3 | 10 | 56.3 ± 15.7 | 36.7 ± 16.5* | 27.4 ± 10.7 |
| Comparative example 5 | 3 | 10 | 56.4 ± 10.6 | 38.7 ± 15.2* | 25.1 ± 11.6 |
| Comparative example 6 | 3 | 10 | 57.1 ± 18.1 | 30.4 ± 12.9* | 20.4 ± 10.2* |
| Comparative example 7 | 3 | 10 | 56.0 ± 17.3 | 24.1 ± 14.1* | 13.7 ± 8.1** |
| Comparative example 8 | 3 | 10 | 56.7 ± 16.6 | 31.7 ± 12.2* | 21.7 ± 8.3 |

PS:
compared with the model group, *P < 0.05; **P < 0.01

3.2 Effects on the Activity of AchE and the Content of Ach in the Brains of Rats After 3 months of the ligation of the bilateral common carotid arteries of rats, the activity of AchE in brains was increased and the content of Ach was decreased, there was significant differences between the sham group and the model group (P<0.01); After 2 months of administration, the activity of AchE in the brains of the rats in the group of Chinese medicinal compositions of the present inventions were significantly decreased (P<0.05), the Ach content of the whole brains of the rats were significantly increased (P<0.01) the same effect was observed in the comparative medicine Huperzine group and the group of the Chinese medicinal composition of comparative example 7 (P<0.05~0.01), the changes were not significant for the activity of AchE in the other groups of Chinese medicinal compositions of comparative examples and Tanakan group, the content of Ach was significantly increased (P<0.05). The results can be seen in table 13.

TABLE 13

Effects on the activity of AchE and the content of Ach in brains of VaD rats ($\bar{X} \pm S$)

| Groups | Doses (g/kg) | n | AchE (U/mgprot) | n | Ach (ng/g wet weight of brain tissue) |
|---|---|---|---|---|---|
| Sham group | | 7 | 0.687 ± 0.077** | 11 | 2687.2 ± 601.8** |
| Model group | | 6 | 1.006 ± 0.214 | 10 | 1354.9 ± 131.6 |
| Huperzine group | 0.00006 | 6 | 0.726 ± 0.106* | 10 | 1992.6 ± 590.0** |

TABLE 13-continued

Effects on the activity of AchE and the content of Ach in brains of VaD rats ($\bar{X} \pm S$)

| Groups | Doses (g/kg) | n | AchE (U/mgprot) | n | Ach (ng/g wet weight of brain tissue) |
|---|---|---|---|---|---|
| Tanakan group | 0.02 | 6 | 0.801 ± 0.162 | 10 | 1646.8 ± 358.7* |
| Example 1 | 3 | 6 | 0.756 ± 0.095* | 10 | 1958.3 ± 511.6** |
| Example 2 | 3 | 6 | 0.769 ± 0.103* | 10 | 1917.4 ± 315.2** |
| Example 5 | 3 | 6 | 0.757 ± 0.146* | 10 | 2022.4 ± 257.1** |
| Example 6 | 3 | 6 | 0.755 ± 0.124* | 10 | 2314.4 ± 412.0** |
| Example 9 | 3 | 6 | 0.708 ± 0.125* | 10 | 2307.1 ± 522.3** |
| Example 11 | 3 | 6 | 0.738 ± 0.137* | 10 | 1998.6 ± 613.7** |
| Comparative example 1 | 3 | 6 | 0.787 ± 0.207 | 10 | 1832.8 ± 312.6* |
| Comparative example 2 | 3 | 6 | 0.768 ± 0.086* | 10 | 1875.7 ± 193.5* |
| Comparative example 3 | 3 | 6 | 0.791 ± 0.164 | 10 | 1623.4 ± 271.4* |

TABLE 13-continued

Effects on the activity of AchE and the content of Ach in brains of VaD rats ($\overline{X} \pm S$)

| Groups | Doses (g/kg) | n | AchE (U/mgprot) | n | Ach (ng/g wet weight of brain tissue) |
|---|---|---|---|---|---|
| Comparative example 4 | 3 | 6 | 0.785 ± 0.157 | 10 | 1536.7 ± 486.5* |
| Comparative example 5 | 3 | 6 | 0.824 ± 0.106 | 10 | 1738.7 ± 375.2* |
| Comparative example 6 | 3 | 6 | 0.957 ± 0.182 | 10 | 1630.4 ± 412.9* |
| Comparative example 7 | 3 | 6 | 0.749 ± 0.134* | 10 | 2124.1 ± 314.1** |
| Comparative example 8 | 3 | 6 | 0.866 ± 0.163 | 10 | 1531.7 ± 212.2* |

PS:
compared with the model group, *P < 0.05; **P < 0.01

3.3 Effects on the Activity of SOD, the Content of MDA of Brain Tissue

After 3 months of the ligation of the bilateral common carotid arteries of rats, the activity of SOD in the brain was significantly decreased, there were significant differences between the sham group and the model group (P<0.01), there were no significant changes for the content of MDA; Compared with the model group, the activity of SOD of the groups of Chinese medicinal compositions of the present invention were increased significantly (P<0.05), there were no significant changes for the activities of SOD for the rest of the groups. Compared with the model group, there were no significant changes for the content of MDA of the brains of the rats of the groups. The results can be seen in table 14.

TABLE 14

Effects on the activity of SOD and the content of MDA in the brains of the VaD rats ($\overline{x} \pm s$)

| Groups | Doses (g/kg) | n | SOD (U/mgprot) | MDA (μmol/mgprot) |
|---|---|---|---|---|
| Sham group | | 7 | 87.1 ± 20.8** | 2.169 ± 0.568 |
| Model group | | 6 | 45.6 ± 13.2 | 2.574 ± 0.811 |
| Huperzine group | 0.00006 | 6 | 51.7 ± 9.6 | 2.194 ± 0.251 |
| Tanakan group | 0.02 | 6 | 57.4 ± 5.3 | 2.121 ± 0.405 |
| Example 1 | 3 | 6 | 75.6 ± 10.5* | 2.255 ± 0.763 |
| Example 2 | 3 | 6 | 69.2 ± 15.3* | 2.241 ± 0.511 |
| Example 5 | 3 | 6 | 68.7 ± 17.1* | 2.085 ± 0.292 |
| Example 6 | 3 | 6 | 72.5 ± 12.4* | 2.314 ± 0.241 |
| Example 9 | 3 | 6 | 78.7 ± 14.6* | 2.127 ± 0.283 |
| Example 11 | 3 | 6 | 70.9 ± 9.2* | 2.396 ± 0.134 |
| Comparative example 1 | 3 | 6 | 60.7 ± 10.7 | 2.134 ± 0.412 |
| Comparative example 2 | 3 | 6 | 62.6 ± 8.6 | 2.187 ± 0.213 |
| Comparative example 3 | 3 | 6 | 50.9 ± 8.1 | 2.323 ± 0.574 |
| Comparative example 4 | 3 | 6 | 58.5 ± 7.1 | 2.536 ± 0.465 |
| Comparative example 5 | 3 | 6 | 42.4 ± 11.6 | 2.538 ± 0.372 |
| Comparative example 6 | 3 | 6 | 49.5 ± 8.9 | 2.164 ± 0.417 |
| Comparative example 7 | 3 | 6 | 60.4 ± 13.4 | 2.127 ± 0.398 |
| Comparative example 8 | 3 | 6 | 56.6 ± 14.1 | 2.517 ± 0.472 |

PS:
compared with the model group, *P < 0.05; **P < 0.01

3.4 Effects on the Plasma NPY, β-EP of Rats

After 3 months of the ligation of the bilateral common carotid arteries of rats, the content of plasma NPY was significantly decreased, the content of β-EP was significantly increased, there were significant differences between the sham group and the model group (P<0.01); 2 months after the administration, the contents of NPY of the rats of the group of the Chinese medicinal composition of the present invention, the group of the Chinese medicinal composition of comparative example 2 and the group of the Chinese medicinal composition of comparative example 7 were significantly increased, the β-EP of each group was significantly decreased (P<0.01 for all), the contents of NPY of the rats of the groups of the Chinese medicinal compositions of the other comparative examples were significantly increased, the β-EP of each group was significantly decreased (P<0.05 for all), the effects were not obvious for the comparative medicine Huperzine and Tanakan. The results can be seen in table 15.

TABLE 15

Effects on the contents of plasma NPγ, β-EP of the VaD rats ($\overline{x} \pm s$)

| Groups | doses (g/kg) | n | NPγ (pg/mL) | β-EP (pg/mL) |
|---|---|---|---|---|
| Sham group | | 11 | 1132.8 ± 61.1** | 743.8 ± 98.5** |
| Model group | | 10 | 885.6 ± 163.2 | 1003.4 ± 63.8 |
| Huperzine group | 0.00006 | 10 | 847.7 ± 189.1 | 1032.9 ± 109.5 |
| Tanakan group | 0.02 | 10 | 841.6 ± 95.3 | 1119.2 ± 176.4 |
| Example 1 | 3 | 10 | 1075.6 ± 120.7** | 770.9 ± 197.8** |
| Example 2 | 3 | 10 | 1069.8 ± 105.2** | 670.2 ± 65.9** |
| Example 5 | 3 | 10 | 988.5 ± 127.1** | 658.9 ± 164.1** |
| Example 6 | 3 | 10 | 1052.5 ± 152.4** | 731.4 ± 212.6** |
| Example 9 | 3 | 10 | 1128.7 ± 84.6** | 587.2 ± 128.1** |
| Example 11 | 3 | 10 | 1094.9 ± 69.2** | 696.7 ± 134.7** |
| Comparative example 1 | 3 | 10 | 920.7 ± 150.8* | 891.3 ± 141.2* |
| Comparative example 2 | 3 | 10 | 992.6 ± 78.6** | 756.7 ± 121.5** |
| Comparative example 3 | 3 | 10 | 940.9 ± 128.1* | 853.3 ± 85.4* |
| Comparative example 4 | 3 | 10 | 958.1 ± 97.1* | 836.7 ± 146.1* |
| Comparative example 5 | 3 | 10 | 942.4 ± 121.6* | 953.2 ± 137.1 |
| Comparative example 6 | 3 | 10 | 949.5 ± 158.9* | 921.6 ± 101.4* |
| Comparative example 7 | 3 | 10 | 980.4 ± 113.4** | 741.2 ± 110.6** |
| Comparative example 8 | 3 | 10 | 956.5 ± 124.7* | 875.1 ± 134.7* |

PS:
compared with the model group, *P < 0.05; **P < 0.01

3.5 Pathological Examination

Pathological examination showed that: The arrangement of the hippocampal pyramidal cell layer of the sham group was almost regular, the structure was compact, and it has multiple layers, the cell nuclear membrane was fresh and smooth. The arrangement of some parts of most of the hippocampal pyramidal cell of the model group was loose, there were wrinkles on the cell nuclear membrane, the nucleolus was relatively small, the structures of part of the pyramidal cells were not clear, stained, they were triangles or agglomerates, there were visible gaps on the surroundings, the nucleolus disappeared. The arrangement of the hippocampal pyramidal cell of the huperzine group was slightly loose, most of the cell nuclease membranes can be seen, a small part of the nucleolus were relatively small, part of the nucleolus dissapeard. For tanakan group, the groups of Chinese medicinal compositions of comparative examples 1~3 and 7, the arrangement of the hippocampal pyramidal cell were neat, the sizes of the cells were acceptable, the nuclear membranes were clear, part of the nucleolus can be seen. The arrangement of most of the hippocampal pyramidal cells of the group of Chinese medicinal composition of the present invention was in an orderly fashion, the structures between the cells were compact, the cell nuclear membranes were relative fresh and the nucleolus were acceptable, and were scattered in the region, with visible wrinkles, stained pyramidal cells. The arrangement of the hippocampal pyramidal cells of the group of Chinese medicinal composition of the comparative example 4 was relatively loose, the cells were relatively small, part of the cells were stained, obscure, unclear boundaries, there were wrinkles for each individual, they were triangles and agglomerates. The arrangement of the hippocampal pyramidal cells of the groups of Chinese medicinal compositions of comparative examples 5~6 and 8 were acceptable, the layers can be seen, the boundaries between the pyramidal cells were not clear, the nuclear membrane was faded, the nucleolus were small, they were in denatured state, and part of them disappeared.

Summary:

Chronic cerebral ischemia is a common pathological process of the development of many diseases such as vascular dementia (VaD), Alzheimer disease (AD) and subcortical arteriosclerotic encephalopathy (Binswanger's disease) and other diseases. Study confirmed that after the ligation of the bilateral common carotid artery (2VO) of rats, blood flow may continue to decline, after three weeks, chronic phase started, after a month, it is still lower than the normal group; neurons that were involved in learning and memory, such as cortex, hippocampus were atrophied, degenerated, depigmented, which means it was progressively aggravated; 3 months after 2VO, the adhesion between the cortex and hippocampus M acetylcholine receptor declined; there was significant obstacles in the behavior such as learning and memory.

Many studies have shown that, after cerebral ischemia, the overload of $Ca^{2+}$ in cells, exitotoxcity and inflammatory reactions can be caused, which further leads to the damage of the function and structure of neurons. Cerebral ischemia and hypoxia can also cause the dysfunction of mitochondrial oxidative metabolism, leading to excess generation of active oxygen radicals, including $O^{-2}$, $HO^{-2}$, $OH^-$, $H_2O_2$ and so on. These active oxygen radicals can react with proteins, lipids, nucleic acid molecules in neurons and destroy their molecular structure, superoxide changes occur, which can further cause damage to the structure and function of brain cells, and generate excess peroxidation products such as malondialdehyde (MDA). The neurons of hippocampus, prefrontal cortex, temporal lobe and cerebral cortex were sensitive to ischemia, and these areas are brain areas that are closely related to learning and memory ability. The damage of the function and structure of these neurons in brains after cerebral ischemia will cause disorder of the neurotransmitters associated with learning and memory, result in a decline in the ability of learning and memory, and even dementia.

2VO prepared VaD model of the present experiment confirmed the above biochemical, pathological and behavioral changes of process, and it was observed that the Chinese medicinal compositions of the present invention can significantly inhibit the activity of AchE, increasing the content of Ach in the brains of the model animals, improving the learning and memory impairment, the medicine can also largely increase the activity of DOS in the brain, eliminating the oxygen free radicals to protect brain tissue, indicating that the groups of the Chinese medicinal compositions of the present invention have significant therapeutic effects for VaD, and the effects are much better than that of the Chinese medicinal compositions of the comparative examples.

It is reported that in the plasma of VaD patients, the content of neuropeptide Y is decreased, the content of β-EP increased, the applicant determined the contents of neuropeptide Y and β-EP of the 2VO prepared model animals, it is consistent with the report, and it is observed that in the group of the Chinese medicinal compositions of the present invention, the plasma neuropeptide Y can largely be increased, and the content of plasma β-EP can be largely decreased.

Pathological examination showed that: Some areas of hippocampus of the model group were arranged loosely, visible shrinks can be seen on nuclear membranes, the nucleolus were relatively small, the structure of part of the pyramidal cells were not clear, stained, they were triangles or agglomerates, visible gaps on the surroundings, the nucleolus were disappeared. Most of the hippocampus pyramidal cells of the groups of the Chinese medicinal compositions of the present invention were orderly arranged, the structures between the cells were compact, the nuclear membrane was fresh, and the degrees of lesions were significantly reduced.

Test Example 9

Effects on Ischemic Reperfusion and Subcutaneous Injection of D-Galactose Induced Learning and Memory Impairment in Mice 1. Experimental Material (1) Animals: ICR mice, 25~32 g, half male and half female. Provided by Beijing Vital River Laboratory Animal Technology Development Company Ltd.

(2) Medicines:

The Chinese medicinal compositions of the present invention and the Chinese medicinal compositions of the comparative examples (self-made, the mixture of the corresponding extracts were prepared according to the methods of the examples and comparative examples of the present invention), were prepared to 0.2 g/mL with distilled water during the experiment (calculated based on the original dose of the composition).

Huperzine (huperzine A tablets), 50 μg/piece, produced by Henan Zhu Lin Zhong Sheng Pharmaceutical Co., Ltd., and was formulated to 4 μg/mL with distilled water during the experiment; tanakan tablets (tanakan), standardized Ginkgo leaf extract (Egb761) 40 mg/tablet, produced by France Beaufort-Ipsen pharmaceutical industry Co., Ltd., and was formulated to 1.5 mg/mL with distilled water during the experiment. D-galactose, produced by Shanghai Hengxin chemical reagent co., LTD; acetylcholinesterase (TCHE) kit; superoxide dismutase (SOD) kit; malondialdehyde (MDA) kit; glutathione peroxidase (GSH-Px) kit; nitric oxide (NO) kits; protein quantitation (biuret method) kit; by Nanjing Jiancheng Bioengineering Center.

(3) Instrument:

MORRIS water maze, produced by Institute of Medicines of Chinese Academy of Medical Sciences. Spectrophotometer, UV-120-02, produced by Shimadzu company, Japan.

2. Experiment Method

The mice were randomly grouped, half male and half female: Sham group, complex model group, D-galactose group, ischemia reperfusion group, Huperzine group, tanakan group, the groups of the Chinese medicinal compositions of the present invention (six groups, the doses were the same as that in test example 2), the groups of the comparative examples (8 groups, the doses were the same as that in test example 2).

The mice were anaesthetized with chloral hydrate, incisions were made in the necks, ischemia and reperfusion surgery was applied: bilateral common carotid arteries were separated, were clipped by bulldog clamp for 20 minutes, loosened for 2 minutes, then were clipped again for 20 minutes then loosened, at the same time, the tails of the mice were cut, 0.5 mL blood was collected, repeated cerebral ischemia-reperfusion injury was formed, sutured the wounds of the rats then fed them in cages. 7 days after the operation, D-galactose (100 mg/kg, 10 mL/kg) was given to the mice through subcutaneous injection on the back, and simultaneously, the mice were intragastric administered (20 mL/kg) once a day, lasted for 8 weeks; for the sham group, common carotid arteries were separated without clipping, the same volume of saline was injected through subcutaneous injection on the back; for D-galactose group, common carotid arteries were separated without clipping, D-galactose (100 mg/kg, 10 mL/kg) was injected through subcutaneous injection on the back; the ischemia reperfusion group was received an ischemia reperfusion operation, the same volume of saline was injected through subcutaneous injection on the back. The sham group, complex model group, D-galactose group were given gavages of distilled water of the same volume.

8 weeks after the administration, the mice were trained for 3 days in the MRRIS water maze, two times a day, the learning and memory behavior were determined on the 4th day, on the 5th day, the heads were cut to take the brains, the brains were formulated into 10% homogenates with saline, the activities of AchE, SOD, GSH-Px, the contents of biochemical indicators such as MDA, NO in the brain tissues were determined (colorimetry). The results were analyzed statistically (t test)

3. Results 3.1 Effects on the Learning and Memory Behavior of Mice in MORRIS Water Maze After 8 weeks of receiving ischemia-reperfusion and subcutaneous injection of D-galactose, the times of duration of swimming and the lengths of paths of swimming for the mice in MORRIS water maze prolonged, there were significant differences compared with the sham group (P<0.01); the search strategies were mostly edge type or random type. Compared with the sham group and the model group, there were no significant differences regarding the times of duration of swimming and the lengths of paths of swimming for the group that only received ischemia-reperfusion, compared with the complex model group, there were significant differences regarding the search strategy (P<0.05); compared with the complex model group, there were no significant differences regarding the time of duration of swimming, the length of path of swimming and the search strategy for the group that only received D-galactose through subcutaneous injection; indicating that the learning and memory impairment of mice can be formed by only subcutaneous injection of D-galactose and ischemia reperfusion damages, but the extents were not as significant as that of the combination of the two; compared with the complex model group, the length of the path of swimming of the comparative medicine huperzine group was decreased, the search strategy was largely improved (P<0.05-0.01); the time of duration of swimming and the length of the path of swimming of tanakan group were significantly decreased (P<0.05~0.01), the search strategy was not largely improved; the time of duration of swimming and the lengths of the path of swimming of the mice of the groups of Chinese medicinal compositions of the present invention were significantly decreased (P<0.05~0.01), the search strategies were largely improved (P<0.01); the time of duration of swimming and the lengths of the path of swimming of the groups of comparative examples 2, 3, 7, 8 were all significantly decreased (P<0.05~0.01), the search strategies were largely improved (P<0.05~0.01); the time of duration of swimming and the lengths of the path of swimming of the groups of comparative examples 1, 4, 5, 6 were all significantly decreased (P<0.05), the search strategies were largely improved. The results can be seen in table 16.

TABLE 16

Effects on the learning and memory behavior of mice in MORRIS water maze ($\bar{x} \pm s$, n = 12)

| Groups | doses (g/kg) | Time of duration (s) | Length of path (cm) | Search strategy |
|---|---|---|---|---|
| Sham group | | 12.8 ± 8.6 | 337.1 ± 254.3 | 2.1 ± 0.5 |
| Complex model group | | 53.7 ± 38.4## | 1193.9 ± 876.7## | 3.4 ± 1.0## |
| Ischemia-reperfusion group | | 52.1 ± 55.9 | 971.3 ± 928.8 | 2.5 ± 1.0* |
| D-galatose group | | 34.7 ± 49.8 | 582.2 ± 765.3 | 2.9 ± 1.1 |
| Huperzine group | 0.00008 | 21.7 ± 14.6* | 355.8 ± 234.1** | 2.4 ± 1.0* |
| Tanakan group | 0.03 | 17.1 ± 10.0** | 436.1 ± 263.2* | 2.8 ± 1.2 |
| Example 1 | 4 | 16.9 ± 12.1** | 364.7 ± 439.8** | 2.1 ± 1.0** |
| Example 2 | 4 | 18.5 ± 16.6* | 345.9 ± 406.0** | 2.2 ± 1.2** |
| Example 5 | 4 | 18.4 ± 10.1* | 375.8 ± 180.9** | 2.1 ± 0.7** |
| Example 6 | 4 | 15.2 ± 15.3** | 347.6 ± 303.3** | 2.2 ± 1.1** |
| Example 9 | 4 | 14.7 ± 13.6** | 341.4 ± 195.6** | 2.2 ± 0.9** |
| Example 11 | 4 | 15.9 ± 9.2** | 367.5 ± 268.8** | 2.1 ± 0.6** |
| Comparative example 1 | 4 | 26.7 ± 15.8* | 394.9 ± 405.5* | 2.6 ± 1.2 |
| Comparative example 2 | 4 | 25.6 ± 28.6* | 406.8 ± 260.4* | 2.2 ± 1.2** |
| Comparative example 3 | 4 | 24.9 ± 12.1* | 434.9 ± 274.8* | 2.4 ± 1.2* |

TABLE 16-continued

Effects on the learning and memory behavior of mice in MORRIS water maze ($\bar{x} \pm s$, n = 12)

| Groups | doses (g/kg) | Time of duration (s) | Length of path (cm) | Search strategy |
|---|---|---|---|---|
| Comparative example 4 | 4 | 25.1 ± 7.1* | 441.2 ± 190.1* | 2.5 ± 1.0 |
| Comparative example 5 | 4 | 34.4 ± 12.6* | 472.1 ± 437.5* | 2.5 ± 1.1 |
| Comparative example 6 | 4 | 30.9 ± 15.8* | 457.3 ± 431.4* | 2.6 ± 0.8 |
| Comparative example 7 | 4 | 18.4 ± 11.3* | 410.8 ± 302.6* | 2.4 ± 1.1** |
| Comparative example 8 | 4 | 36.5 ± 12.7* | 427.1 ± 341.2* | 2.5 ± 1.0* |

PS:
①search strategy: straight line type 1 point; tendency type 2 points; edge type 3 points; random type 4 points;
②compared with the sham group, *P < 0.05, **P < 0.01;
③ compared with the model group, *P < 0.05, **P < 0.01.

3.2 Effects on the Activities of SOD, GSH-Px and the Contents of MDA and NO of Brain Tissue After 8 weeks of receiving ischemia-reperfusion and subcutaneous injection of D-galactose, for the brain tissue of the mice (complex group), the activities of SOD, GSH-Px were decreased, and the contents of MDA, NO were increased, there were significant differences compared with the sham group (P<0.05~0.01); for the group that only received D-galactose through subcutaneous injection, for the brain tissue, the activities of SOD, GSH-Px were decreased, and the contents of MDA, NO were increased, there were significant changes compared with the sham group (P<0.05~0.01 for all), there were no significant changes compared with the complex model group; for the group that only received ischemia-reperfusion, compared with the sham group, for the brain tissue, the activities of SOD, GSH-Px and the contents of MDA, NO were decreased (P<0.05), compared with the sham group, there were no significant changes for the contents of MDA. Compared with the complex model group, there were no significant changes for the activities of SOD, GSH-PX and the contents of MDA, NO of the comparative medicine huperzine group; for the tanakan group, the activities of SOD, GSH-PX were significantly increased, and the contents of MDA, NO were significantly decreased (P<0.05~0.01); for the group of the Chinese medicinal compositions of the present invention, the activities of SOD, GSH-PX were significantly increased, and the contents of MDA, NO were significantly decreased (P<0.05~0.01); for the groups of the Chinese medicinal composition of the comparative examples 1~3, 7, for the brain tissue of mice, the activities of SOD were significantly increased, the contents of NO were significantly decreased (P<0.05 for all), there were no significant changes for the activities of GSH-Px and the contents of MDA; for the groups of comparative examples 4~6, 8, the contents of NO were significantly decreased (P<0.05 for all), there were no significant changes for the activities of SOD, GSH-PX and the contents of MDA. The results can be seen in table 17.

TABLE 17

Effects on the activities of SOD, GSH-Px and the contents of MDA and NO of brain tissue ($\bar{x} \pm s$, n = 12)

| Groups | doses (g/kg) | SOD (U/mgprot) | GSH-Px (U/mgprot) | MDA (nmol/mgprot) | NO (nmol/mgprot) |
|---|---|---|---|---|---|
| Sham group |  | 170.2 ± 12.8 | 31.22 ± 2.87 | 4.194 ± 0.703 | 1.181 ± 0.190 |
| Complex model group |  | 151.2 ± 12.1## | 27.45 ± 3.67# | 5.127 ± 1.010# | 1.694 ± 0.374## |
| D-galactose group |  | 156.3 ± 15.3# | 27.90 ± 2.06## | 5.099 ± 0.819# | 1.426 ± 0.231# |
| Ischemica-reperfusion group |  | 153.3 ± 21.4# | 28.06 ± 3.25# | 4.661 ± 0.770 | 1.419 ± 0.276# |
| Huperzine group | 0.00008 | 159.8 ± 21.2 | 28.58 ± 2.87 | 4.651 ± 0.832 | 1.442 ± 0.295 |
| Tanakan group | 0.03 | 163.8 ± 14.0* | 30.40 ± 2.47* | 4.261 ± 0.484* | 1.299 ± 0.169** |
| Example 1 | 4 | 162.5 ± 22.5* | 29.12 ± 4.40* | 4.382 ± 0.519* | 1.310 ± 0.278** |
| Example 2 | 4 | 166.6 ± 18.6* | 30.75 ± 2.43* | 4.234 ± 0.536* | 1.305 ± 0.348** |
| Example 5 | 4 | 169.1 ± 20.0** | 30.65 ± 2.86* | 4.206 ± 0.676* | 1.280 ± 0.279** |
| Example 6 | 4 | 165.2 ± 14.7* | 30.40 ± 2.47* | 4.345 ± 0.530* | 1.235 ± 0.164** |
| Example 9 | 4 | 169.7 ± 13.2** | 29.12 ± 4.40* | 4.144 ± 0.953* | 1.212 ± 0.917** |
| Example 11 | 4 | 165.9 ± 19.3* | 30.75 ± 2.43* | 4.367 ± 0.426* | 1.251 ± 0.716** |
| Comparative example 1 | 4 | 161.6 ± 15.4* | 28.37 ± 3.14 | 4.894 ± 0.240 | 1.426 ± 0.542* |
| Comparative example 2 | 4 | 163.2 ± 25.6* | 28.87 ± 2.47 | 4.606 ± 0.560 | 1.379 ± 0.741* |
| Comparative example 3 | 4 | 164.9 ± 12.7* | 28.52 ± 1.67 | 4.734 ± 0.746 | 1.407 ± 0.512* |
| Comparative example 4 | 4 | 160.1 ± 8.2 | 28.89 ± 3.61 | 4.841 ± 0.219 | 1.385 ± 0.179* |
| Comparative example 5 | 4 | 158.4 ± 11.4 | 28.14 ± 3.26 | 4.972 ± 0.445 | 1.395 ± 0.425* |
| Comparative example 6 | 4 | 160.4 ± 10.6 | 28.76 ± 2.71 | 4.907 ± 0.343 | 1.436 ± 0.821* |

TABLE 17-continued

Effects on the activities of SOD, GSH-Px and the contents of MDA and NO of brain tissue ($\bar{x} \pm s$, n = 12)

| Groups | doses (g/kg) | SOD (U/mgprot) | GSH-Px (U/mgprot) | MDA (nmol/mgprot) | NO (nmol/mgprot) |
|---|---|---|---|---|---|
| Comparative example 7 | 4 | 164.4 ± 14.3* | 28.64 ± 1.83 | 4.608 ± 0.306 | 1.367 ± 0.156* |
| Comparative example 8 | 4 | 157.6 ± 9.3 | 28.61 ± 3.51 | 4.927 ± 0.642 | 1.424 ± 0.634* |

PS:
compared with the sham group, *P < 0.05, **P < 0.01;
compared with the complex model group, *P < 0.05, **P < 0.01

3.3 Effects on the Activity of AchE of Brain Tissue

After 8 weeks of receiving ischemia-reperfusion and subcutaneous injection of D-galactose, for the brain tissue of the mice (complex group), the activity of AchE was significantly increased, there were significant differences compared with the sham group (P<0.01); For the group that only received subcutaneous injection of D-galactose and the group that only received ischemia-reperfusion, the activities of AchE of the brain tissues were increased, there were significant differences compared with the sham group (P<0.05), there were no significant differences compared with the complex model group. Compared with the complex model group, the activities of AchE of the groups of the Chinese medicinal compositions of the present invention, the groups of the Chinese medicinal compositions of the comparative examples 1-3, 7 (P<0.05); there were no significant changes for the activities of AchE of the groups of the Chinese medicinal compositions of the comparative examples 4~6, 8. The results can be seen in table 18.

TABLE 18

Effects on the activity of AchE of the brain tissue ($\bar{x} \pm s$, n = 10)

| Groups | doses (g/kg) | AchE (U/mgprot) |
|---|---|---|
| Sham group | | 0.658 ± 0.107 |
| Complex model group | | 0.902 ± 0.153## |
| D-galactose group | | 0.813 ± 0.140# |
| Ischemia reperfusion group | | 0.814 ± 0.163# |
| Huperzine group | 0.00008 | 0.729 ± 0.134* |
| Tanakan group | 0.03 | 0.780 ± 0.105 |
| Example 1 | 4 | 0.708 ± 0.085* |
| Example 2 | 4 | 0.743 ± 0.118* |
| Example 5 | 4 | 0.696 ± 0.173* |
| Example 6 | 4 | 0.715 ± 0.127* |
| Example 9 | 4 | 0.681 ± 0.141* |
| Example 11 | 4 | 0.729 ± 0.094* |
| Comparative example 1 | 4 | 0.741 ± 0.104* |
| Comparative example 2 | 4 | 0.732 ± 0.086* |
| Comparative example 3 | 4 | 0.739 ± 0.077* |
| Comparative example 4 | 4 | 0.760 ± 0.092 |
| Comparative example 5 | 4 | 0.785 ± 0.115 |
| Comparative example 6 | 4 | 0.754 ± 0.126 |
| Comparative example 7 | 4 | 0.789 ± 0.123* |
| Comparative example 8 | 4 | 0.773 ± 0.119 |

PS:
compared with the sham group *P < 0.05, **P < 0.01;
compared with the complex model group *P < 0.05, **P < 0.01

Summary: The exact mechanism of the cerebral ischemia reperfusion injury is not clear, most of the scholars believe that it is related to the cascade reaction induced by the increase of oxygen free radicals. Under normal conditions, there are very small amount of oxygen free radicals that are formed and their lives are short, therefore, they do not cause danger to the body, wherein the endogenous oxygen free radical scavangers play a very important role. Glutathione peroxidase (GSH-Px) is an important enzyme decomposed by catalytic hydroxyl free radicals; SOD is the representative of endogenous oxygen free radical scavenger, to a certain extent, its vitality reflects the scavenging vitality of the endogenous oxygen free radicals; the main metabolite MDA generated by membrane lipid degradation is usually used as an indicator of lipid peroxidation, NO is the an extremely important messenger of body, and has a dual role in the process of cerebral ischemia, in one hand, it can reduce the area of infarction, increase cortical blood supply, on the other hand, it can generate a synergistic effect with the oxygen free radicals produced by ischemia, result in damage of nerve cells. Monitoring the level of SOD, GSH-Px, MDA, NO of brain tissue is important for the study of cerebral ischemia-reperfusion injury.

D-galactose subacute aging model is built by the following process: giving the mice large doses of D-galactose continuously through subcutaneous injection to cause glucose metabolism disorder of the animals. Under the catalysis of D-galactose oxidase, oxygen free radicals such as superoxide anion can be generated by D-galactose. Oxygen free radicals are highly reactive, can attack the unsaturated fatty acids, proteins, enzymes of the membrane phospholipids and DNA within the nucleus etc.; the free radicals can also allow the lipids to carry out peroxidation to form lipid peroxide (LPO), MDA is generated under acidic condition after the precipitation of LPO with protein, MDA is an active crosslinker, it can quickly generate a fluorescent dye with phosphatidylethanolamine, and then form lamellar lipofuscin (LF) with proteins, peptides, lipids. With the continuous injection of D-galactose, the mice can produce changes of a number of biochemical indicators, such as the increase of brain tissue MDA, the content of LF; the decrease of brain SOD, blood GSH-Px, erythrocyte CAT activities, and these changes are consistent with natural aging changes, indicating that D-galactose can cause the aging of cells and organisms. SOD, GSH-Px, CAT activities indirectly reflect the body's ability to eliminate oxygen free radicals; and the levels of MDA, LF indirectly reflect the severity of the level of the attacks of free radicals to the cells.

In this experiment, mice with cerebral ischemia reperfusion injury combined with subcutaneous injection of D-galactose were caused brain injury, then the activity of AchE was significantly enhanced, thus cognitive impairment appeared, the spatial learning ability was decreased; it is also observed in the test that for the brain tissue of the mice of the complex model, the activities of SOD, GSH-Px were significantly decreased, the contents of MDA, NO were significantly increased. After the mice were given a gavage of the Chinese medicinal compositions of the present invention, for the brain tissue of the mice, the activity of AchE was decreased, the activities of SOD, GSH-Px were significantly enhanced, the contents of MDA, NO were significantly decreased, the spatial learning ability was significantly enhanced, indicating that the Chinese medicinal compositions of the present invention have inhibiting effects of the generation of the reactive oxygen and lipid peroxidation caused by ischemia reperfusion, thus preventing irreversible damage to nerve cells, thus improving the ability of learning and memory, and the efficacy of the Chinese medicinal compositions of the present invention are better than that of the Chinese medicinal compositions of the comparative examples.

Test Example 10

Effects on Multi-Infarct Dementia (MID) Model Rats

1. Experimental Material (1) Animals: SD rats, male, weight 260-280 g, provided by Beijing Vital River Laboratory Animal Technology Development Company Ltd.

(2) Medicines:

The Chinese medicinal compositions of the present invention and the Chinese medicinal compositions of the comparative examples (self-made, the mixture of the corresponding extracts were prepared according to the methods of the examples and comparative examples of the present invention), were prepared to 0.15 g/mL with distilled water during the experiment (calculated based on the original dose of the composition). Tanakan tablets (tanakan), standardized Ginkgo leaf extract (Egb761) 40 mg/tablet, produced by France Beaufort-Ipsen pharmaceutical industry Co., and was formulated to 2.0 mg/mL with distilled water during the experiment. Sodium alginate microspheres vascular embolization agent (KMG), size: 100~200 μm, Beijing Sheng Yi Yao Technology Development Co., Ltd.; somatostatin (SS) radioimmunoassay kit, neuropeptide Y (NPY), provided by naval RIA technology center; calcitonin gene-related peptide (CGRP) radioimmunoassay kit, Beijing Furui bio-engineering company, endothelin (ET), provided by Beijing Bei Mian Dong Ya Institute of biotechnology. Norepinephrine (NE), dopamine (DA), 3,4-dihydroxyphenyl acetic acid (DOPAC), homovanillic acid (HVA), 5-hydroxytryptamine (5-HT), 5-hydroxy indole acetic acid (5-HIAA), sodium dihydrogen phosphate (of $NaH_2PO_4$), citric acid, sodium thiosulfate ($Na_2S_2O_5$), ethylene diamine tetraacetic acid tetrasodium salt (EDTA), all were AR grade; sodium octanesulfonate (OSA), HPLC grade, they were all the products of Sigma company, USA; acetonitrile (ACN), perchloric acid ($HClO_4$), they were all HPLC grade, products of Fisher Scientific company, USA.

(3) Instrument:

Ultracentrifuge (Japan HITACHI 55P-72); 16-channels Coularray Cullen array electrochemical high performance liquid chromatography and chromatography workstation, 580 pumps, 5600 A electrochemical detector, auto sampler 542, products of ESA company, USA; columns (C1815×4.6 mm 5 μm), products of WATERS company, USA. Cryogenic refrigerators, products of JOUAN company, France; syringe microporous membrane filter: aqueous (0.22 μm), product of Tianjin Tengda filter factory. MORRIS water maze, produced by Institute of Medicines of Chinese Academy of Medical Sciences. FT-630Gγ-counter, produced by Beijing nuclear plant.

(4) Chromatographic Conditions:

Mobile phase composition: sodium dihydrogen phosphate 90 mmol/L, citric acid 50 mmol/L, sodium octanesulfonate 1.7 mmol/L, ethylene diamine tetraacetic acid tetrasodium salt (EDTA) 0.05 μmol/L. The solution was filtered with 0.2 um water membrane. Acetonitrile (10%) was added to the filtrate. The flow rate of the mobile phase was 0.6 mL/min, the working electrode 1: −150 mV, the working electrode 2: 450 mV, the working electrode 3: 500 mV, the working electrode 4: 550 mV.

Preparation of a standard solution: stock solution (100 μg/mL) was prepared with 0.1 mol/L perchloric acid and standard substance, stored at a refrigerator at −70° C. The stock solution was diluted to 10 μg/mL as a diluent. The dilution was formulated into solution with series concentrations to be used as standard solutions. 0.15 mol/L perchloric acid (0.04% sodium metabisulfite and 0.04% EDTA were contained) was used as the working fluid.

2. Experiment Method

Rats received intraperitoneal anesthesia with chloral hydrate (350 mg/kg), the hair of the neck was shaved, disinfected, the rats received an incision in the middle of the neck, the common carotid artery, internal carotid artery and external carotid artery were separated. The external carotid artery received a ligation, the common carotid artery was clipped by a bulldog clamp, 0.1 mL KMG was injected into the internal carotid artery by a syringe from the external carotid artery, the bulldog clamp was released, the external carotid artery received an ligation, sutured the wounds of the rats and fed them in cages. For the sham group, only the common carotid artery, internal carotid artery and external carotid artery were separated, no microspheres were injected. Penicillin sodium for injection was used for anti-inflection for 4 days. The next day after the surgery, the behavior of the animals were observed, if there were behavior changes of the forelimbs, then the models were successfully created (otherwise the rats were discarded), and the rats were divided into model group, tanakan 20 mg/kg group, the groups of the Chinese medicinal compositions of the present invention (6 groups, the doses were the same as that of test example 1), the groups of comparative examples (8 groups, the doses were the same as that of test example 1).

10 days after the surgery, the rats were intragastric administered, the sham group and the model group were all received gavages of distilled water of the same volume, once a day, lasted for 90 days. 40, 100 days after the models were created (30, 90 days after the administration), the time of duration and the lengths of path for the rats to search for platform in the MORRIS water maze were determined, 60 minutes after the last administration, the rats received intraperitoneal anesthesia with chloral hydrate and blood was taken from aorta abdominalis, anti-coagulated, the plasma was separated, and the heads were quickly cut to take the brains out, the cortex, hippocampus, striatum were separated, weighed, solidified with liquid nitrogen, stored in a refrigerator at the temperature of −70° C. For each 100 mg brain tissue, 1 mL cold working fluid was added, the combinations were homogenized with electronic homogenizer for 15 s in ice bath (11000 turn/min), 0-4° C. 14000 rpm centrifuged for 20 minutes, the supernatant was extracted, filtered with 0.22 μm membrane and syringes type filter, the filtrate was separated stored at a refrigerator at −20° C. 10 μl was fed each time with the auto sampler, the contents of the monoamine neurotransmitters such as 5-HT, 5-HIAA, NE, DA and so on were determined with HPLC (HPLC-ECD method). Plasma ET, NPY, SS, CGRP were determined (RIA). The results were analyzed statistically (t test).

3. Results

3.1 Effects on the Cerebral Cortex, Striatum, Hippocampus Weight

After the injection of biomicrosphere, the microspheres entered into the brain blood with the blood flow, after 24 h, they can form multiple cerebral infarctions with different sizes that are mainly in the region of the cortex, hippocampus, striatum. After 100 days, for the model group, the infarct were liquefied and necrosis of the infarct happened, cavities appeared, the brain tissue were shrinked, the hippocampus was smaller, the cortical was thinner, the weight was decreased, compared with the model group, there were significant differences for the sham group (P<0.05~0.01), compared with the model group, for the groups of the Chinese medicinal compositions of the present invention and the Chinese medicinal compositions of the comparative examples, the weights of the cerebral cortex of the rats were increased, but there were no statistical significance, for the groups of the Chinese medicinal compositions of the present invention, the weights of the striatum, hippocampus were significantly increased (P<0.05); for the comparative medicine tanakan group and the groups of the Chinese medicinal compositions of the comparative examples, the weights of the cerebral cortex, striatum, hippocampus of rats were all increased, but there was no statistically significance. See table 19.

TABLE 19

Effects on the weights of the cerebral cortex, striatum, hippocampus of MID rats ($\bar{x} \pm s$, n = 10)

| Groups | Doses (g/kg) | Cerebral cortex | Striatum | Hippocampus |
|---|---|---|---|---|
| Sham group | | 0.464 ± 0.084** | 0.072 ± 0.007* | 0.087 ± 0.022* |
| Model group | | 0.325 ± 0.044 | 0.052 ± 0.020 | 0.064 ± 0.015 |
| Tanakan group | 0.02 | 0.347 ± 0.069 | 0.061 ± 0.021 | 0.069 ± 0.007 |
| Example 1 | 3 | 0.348 ± 0.094 | 0.070 ± 0.016* | 0.085 ± 0.018* |
| Example 2 | 3 | 0.341 ± 0.028 | 0.071 ± 0.009* | 0.084 ± 0.008* |
| Example 5 | 3 | 0.357 ± 0.051 | 0.070 ± 0.007* | 0.084 ± 0.017* |
| Example 6 | 3 | 0.355 ± 0.062 | 0.072 ± 0.011* | 0.086 ± 0.012* |
| Example 9 | 3 | 0.376 ± 0.025 | 0.074 ± 0.006* | 0.087 ± 0.017* |
| Example 11 | 3 | 0.348 ± 0.067 | 0.070 ± 0.017* | 0.085 ± 0.013* |
| Comparative example 1 | 3 | 0.326 ± 0.031 | 0.054 ± 0.024 | 0.070 ± 0.024 |
| Comparative example 2 | 3 | 0.347 ± 0.052 | 0.063 ± 0.013 | 0.078 ± 0.022 |
| Comparative example 3 | 3 | 0.337 ± 0.064 | 0.064 ± 0.015 | 0.074 ± 0.014 |
| Comparative example 4 | 3 | 0.328 ± 0.071 | 0.057 ± 0.012 | 0.074 ± 0.010 |
| Comparative example 5 | 3 | 0.334 ± 0.064 | 0.053 ± 0.019 | 0.065 ± 0.011 |
| Comparative example 6 | 3 | 0.327 ± 0.048 | 0.054 ± 0.012 | 0.072 ± 0.010 |
| Comparative example 7 | 3 | 0.356 ± 0.057 | 0.063 ± 0.014 | 0.077 ± 0.008 |
| Comparative example 8 | 3 | 0.329 ± 0.076 | 0.057 ± 0.008 | 0.067 ± 0.013 |

PS:
Compared with the model group *P < 0.05; **P < 0.01

3.2 Effects on the Time of Duration in the MORRIS Water Maze

Compared with the model group, for the sham model group, the time of duration in the water maze was significantly decreased (P<0.05); 30 days after the administration, compared with the model group, for the groups of the Chinese medicinal compositions of the present invention, the time of duration in the water maze was significantly decreased (P<0.05), there were no significant changes for the other groups; 90 days after the administration, for the groups of the Chinese medicinal compositions of the present invention, the time of duration in the water maze was significantly decreased (P<0.05~0.01), compared with the model group, for the groups of the comparative examples 1~3 and 7, the time of duration in the water maze was significantly decreased (P<0.05), there were no significant changes for the other groups. See table 20.

TABLE 20

Effects on the time of duration of MID rats in the MORRIS water maze ($\bar{x} \pm s$)

| Groups | Doses (g/kg) | Times of duration (s) 30 days | 90 days |
|---|---|---|---|
| Sham group | | 14.0 ± 7.27** | 12.5 ± 13.8** |
| Model group | | 65.1 ± 50.5 | 79.1 ± 66.6 |
| Tanakan group | 0.02 | 44.9 ± 42.4 | 45.7 ± 50.4 |
| Example 1 | 3 | 39.3 ± 33.1* | 28.3 ± 21.3* |
| Example 2 | 3 | 35.4 ± 16.9* | 26.9 ± 14.9* |
| Example 5 | 3 | 25.7 ± 21.1* | 19.0 ± 10.7** |
| Example 6 | 3 | 36.5 ± 26.2* | 24.8 ± 11.6* |
| Example 9 | 3 | 21.6 ± 12.5* | 17.7 ± 12.6** |
| Example 11 | 3 | 34.6 ± 23.7* | 27.0 ± 16.7* |
| Comparative example 1 | 3 | 43.1 ± 33.7 | 34.5 ± 18.2* |
| Comparative example 2 | 3 | 41.2 ± 32.1 | 23.3 ± 23.1* |
| Comparative example 3 | 3 | 48.8 ± 13.7 | 30.3 ± 25.4* |
| Comparative example 4 | 3 | 42.6 ± 32.1 | 42.5 ± 18.7 |
| Comparative example 5 | 3 | 53.4 ± 36.3 | 46.1 ± 27.9 |
| Comparative example 6 | 3 | 49.3 ± 24.8 | 54.2 ± 35.2 |
| Comparative example 7 | 3 | 40.6 ± 25.2 | 25.6 ± 14.5* |
| Comparative example 8 | 3 | 52.9 ± 17.6 | 39.7 ± 34.8 |

PS:
Compared with the model group *P < 0.05; **P < 0.01

3.3 Effects the Content of Plasma ET, NPY, SS, CGRP 100 days after the models were created, compared with the model group, for the sham group, the content of the plasma NPY of the animals was significantly increased, the content of ET was significantly decreased (P<0.01 for all), the contents of SS and CGRP were increased but there were no statistical significance (P<0.01); 100 days after the models were created (90 days after the administration), compared with the model group, for the groups of the Chinese medicinal compositions of the present invention, the contents of NPY and SS were significantly increased (P<0.01), the contents of ET were significantly decreased (P<0.05), there were no significant changes for the contents of CGRP; for the groups of the Chinese medicinal compositions of the comparative examples 1~3 and 7, the contents of NPY and SS were significantly increased (P<0.05~0.01), the contents of ET had the tendencies of decreasing, there were no significant changes for the content of CGRP; for the groups of the Chinese medicinal compositions of the comparative examples 4~6 and 8, the contents of NPY and SS had tendencies to increase, the contents of ET had tendencies to decrease, there were no significant changes for the content of CGRP; for the comparative medicine tanakan group, the contents of NPY and SS were significantly increased (P<0.01), the content of ET was significantly decreased (P<0.01), there were no significant changes for the content of CGRP. See table 21.

TABLE 21

Effects the contents of Plasma ET, NPY, SS, and CGRP ($\bar{x} \pm s$, n = 10)

| Groups | Doses (g/kg) | NPY (pg/mL) | SS (pg/mL) | ET (pg/mL) | CGRP (pg/mL) |
|---|---|---|---|---|---|
| Sham group | | 516.15 ± 42.61** | 90.22 ± 13.07 | 56.04 ± 4.84** | 26.27 ± 3.44 |
| Model group | | 339.14 ± 62.62 | 72.25 ± 30.11 | 71.05 ± 15.20 | 22.41 ± 10.77 |
| Tanakan group | 0.02 | 479.42 ± 144.03* | 107.38 ± 33.37* | 47.36 ± 12.78** | 21.06 ± 5.16 |
| Example 1 | 3 | 492.61 ± 32.81** | 102.64 ± 12.56** | 58.15 ± 11.03* | 23.88 ± 4.66 |
| Example 2 | 3 | 501.36 ± 48.73** | 104.73 ± 16.43** | 54.23 ± 8.36* | 24.32 ± 10.42 |
| Example 5 | 3 | 497.47 ± 70.23** | 113.65 ± 14.81** | 54.20 ± 6.76* | 22.53 ± 6.79 |
| Example 6 | 3 | 505.26 ± 34.79** | 108.40 ± 18.67** | 56.34 ± 4.53* | 23.55 ± 7.16 |
| Example 9 | 3 | 509.57 ± 63.12** | 119.12 ± 24.42** | 53.14 ± 9.23* | 21.62 ± 5.91 |
| Example 11 | 3 | 485.99 ± 29.73** | 103.75 ± 10.35** | 57.37 ± 11.26* | 25.17 ± 8.71 |
| Comparative example 1 | 3 | 461.21 ± 15.42* | 104.73 ± 40.14* | 64.94 ± 10.14 | 24.26 ± 6.42 |
| Comparative example 2 | 3 | 473.26 ± 23.79** | 101.87 ± 17.42** | 61.06 ± 15.36 | 23.79 ± 3.71 |
| Comparative example 3 | 3 | 424.93 ± 11.86* | 98.52 ± 11.67* | 67.21 ± 10.72 | 24.03 ± 5.12 |
| Comparative example 4 | 3 | 390.15 ± 17.23 | 88.89 ± 3.65 | 64.41 ± 7.21 | 23.85 ± 10.17 |
| Comparative example 5 | 3 | 378.41 ± 81.27 | 82.34 ± 5.26 | 69.42 ± 3.41 | 21.35 ± 7.42 |
| Comparative example 6 | 3 | 372.15 ± 31.65 | 77.36 ± 9.81 | 65.07 ± 8.35 | 24.36 ± 9.82 |
| Comparative example 7 | 3 | 484.36 ± 24.3** | 107.64 ± 16.31** | 60.81 ± 17.26 | 23.62 ± 6.15 |
| Comparative example 8 | 3 | 357.16 ± 19.63 | 78.64 ± 13.83 | 70.24 ± 7.48 | 21.42 ± 5.67 |

PS:
Compared with model group *P < 0.05; **P < 0.01

3.4 Effects on the Monoamine Neurotransmitter of Brains (1) Effects on the Cortex Monoamine Neurotransmitter 100 days after the models were created, compared with the model group, for the sham group, the contents of 5-HT, 5-HIAA of the cortex of rats were significantly increased (P<0.05), the contents of NE and DA were increased, but there were no statistical significance; for the groups of the Chinese medicinal compositions of the present invention, the contents of 5-HT were significantly increased (P<0.01), the contents of DA and 5-HIAA were all significantly increased (P<0.05); for the groups of the Chinese medicinal compositions of the comparative examples 1~3 and 7, the contents of DA and 5-HT were significantly increased (P<0.05); for the groups of the Chinese medicinal compositions of the comparative examples 4~6 and 8, the contents of 5-HT were significantly increased, but there were no statistical differences; for the comparative medicine tanakan group, the contents of 5-HT and 5-HIAA were significantly increased (P<0.01), there were no significant changes for the other indicators. See table 22.

TABLE 22

Effects on the level of cortex monoamine neurotransmitter of MID rats ($\bar{x} \pm s$, n = 10)

| Groups | Doses (g/kg) | NE (ng/g brain weight) | DA (ng/g brain weight) | 5-HIAA (ng/g brain weight) | 5-HT (ng/g brain weight) |
|---|---|---|---|---|---|
| Sham group | | 607.8 ± 217.1 | 1939.0 ± 495.0 | 221.2 ± 117.8* | 256.7 ± 145.2* |
| Model group | | 530.8 ± 89.7 | 1526.2 ± 358.5 | 124.3 ± 39.5 | 113.2 ± 40.0 |
| Tanakan group | 0.02 | 586.0 ± 198.4 | 1888.3 ± 812.7 | 252.2 ± 120.1** | 294.2 ± 85.4** |
| Example 1 | 3 | 548.5 ± 152.1 | 2033.6 ± 420.6* | 267.5 ± 176.4* | 317.7 ± 176.6** |
| Example 2 | 3 | 543.2 ± 128.3 | 2204.5 ± 316.4* | 224.1 ± 128.7* | 301.3 ± 110.2** |
| Example 5 | 3 | 567.9 ± 170.5 | 2113.6 ± 461.5* | 214.2 ± 96.2* | 322.6 ± 76.7** |
| Example 6 | 3 | 582.6 ± 104.6 | 2159.4 ± 618.2* | 256.4 ± 184.3* | 282.5 ± 97.1** |
| Example 9 | 3 | 579.3 ± 93.8 | 2289.7 ± 524.6* | 213.7 ± 59.4* | 332.0 ± 110.2** |
| Example 11 | 3 | 585.1 ± 119.2 | 2237.1 ± 210.3* | 227.6 ± 111.8* | 325.1 ± 68.5** |
| Comparative example 1 | 3 | 561.5 ± 164.9 | 2004.8 ± 340.1* | 164.4 ± 120.6 | 224.6 ± 126.2* |
| Comparative example 2 | 3 | 572.0 ± 142.1 | 2218.6 ± 786.4* | 141.2 ± 58.8 | 252.1 ± 121.8* |
| Comparative example 3 | 3 | 542.3 ± 131.5 | 2098.2 ± 351.8* | 178.9 ± 90.2 | 216.3 ± 75.3* |
| Comparative example 4 | 3 | 532.3 ± 184.6 | 1910.3 ± 796.6 | 173.7 ± 50.9 | 163.5 ± 110.6 |
| Comparative example 5 | 3 | 537.1 ± 81.7 | 1982.1 ± 245.2 | 136.5 ± 73.4 | 201.2 ± 107.42 |
| Comparative example 6 | 3 | 572.4 ± 139.7 | 1877.3 ± 419.7 | 165.6 ± 68.1 | 184.5 ± 49.9 |
| Comparative example 7 | 3 | 584.4 ± 123.6 | 2107.4 ± 516.1* | 186.8 ± 79.3 | 273.9 ± 164.5* |
| Comparative example 8 | 3 | 557.1 ± 159.0 | 1878.7 ± 673.8 | 150.2 ± 47.2 | 171.2 ± 55.7 |

PS:
Compared with the model group *P < 0.05; **P < 0.01

(2) Effects on the Monoamine Neurotransmitters of the Striatum 100 days after the models were created, compared with the model group, for the sham group, the contents of 5-HT and 5-HIAA of the striatum of rats were significantly increased (P<0.05), indicating that the models were successfully created; 100 days after the creation of the models (90 days after the administration), compared with the model group, for the groups of the examples 5 and 9 of the present invention, the contents of 5-HT were significantly increased (P<0.05), for the groups of the examples 1, 2, 6, and 11 of the present invention, the contents of 5-HIAA were significantly increased (P<0.05); for the groups of the Chinese medicinal compositions of the comparative examples and the comparative medicine tanakan group, there were no significant changes for the contents of 5-HT and 5-HIAA. See table 23.

TABLE 23

Effects on the level of monoamine neurotransmitters of the striatum of MID rats ($\bar{x} \pm s$, n = 10)

| Groups | Doses (g/kg) | 5-HT (ng/g brain weight) | 5-HIAA (ng/g brain weight) |
|---|---|---|---|
| Sham group | | 214.7 ± 52.5* | 107.4 ± 43.0* |
| Model group | | 156.6 ± 29.5 | 162.8 ± 46.7 |
| Tanakan group | 0.02 | 169.6 ± 91.1 | 146.7 ± 60.7 |
| Example 1 | 3 | 167.0 ± 55.9 | 109.8 ± 42.7* |
| Example 2 | 3 | 181.8 ± 110.1 | 97.6 ± 49.2* |
| Example 5 | 3 | 219.6 ± 66.6* | 137.5 ± 50.1 |
| Example 6 | 3 | 185.4 ± 37.0 | 116.4 ± 37.3* |
| Example 9 | 3 | 232.0 ± 87.4* | 93.7 ± 59.4* |
| Example 11 | 3 | 165.1 ± 68.5 | 107.6 ± 57.6* |
| Comparative example 1 | 3 | 174.6 ± 76.3 | 134.2 ± 60.1 |
| Comparative example 2 | 3 | 192.1 ± 115.7 | 145.7 ± 58.8 |
| Comparative example 3 | 3 | 186.3 ± 45.2 | 138.3 ± 72.5 |
| Comparative example 4 | 3 | 163.5 ± 110.6 | 153.7 ± 50.2 |
| Comparative example 5 | 3 | 161.2 ± 97.2 | 138.2 ± 61.4 |
| Comparative example 6 | 3 | 182.9 ± 128.7 | 145.6 ± 28.9 |
| Comparative example 7 | 3 | 184.5 ± 104.1 | 126.8 ± 79.3 |
| Comparative example 8 | 3 | 168.2 ± 74.3 | 157.2 ± 67.8 |

PS:
Compared with model group, *P < 0.05; **P < 0.01

(3) Effects on the Monoamine Neurotransmitters of the Hippocampus 100 days after the models were created (90 days after the administration), compared with the model group, for the sham group, the contents of DA, 5-HT and 5-HIAA of the hippocampus of rats were significantly increased (P<0.05~0.01), the content of NE was increased, but there was no statistical significance; for the groups of the Chinese medicinal compositions of the present invention, the contents of NE, DA and 5-HT were significantly increased (P<0.05~0.01); for the groups of the Chinese medicinal compositions of the comparative examples, the contents of 5-HT were significantly increased (P<0.05); for the comparative medicine tanakan group, there were no significant changes for every indicators. See table 24.

TABLE 24

Effects on the monoamine neurotransmitters of the hippocampus of MID rats ($\bar{x} \pm s$, n = 10)

| Groups | Doses (g/kg) | NE (ng/g brain weight) | DA (ng/g brain weight) | 5-HIAA (ng/g brain weight) | 5-HT (ng/g brain weight) |
|---|---|---|---|---|---|
| Sham group | | 1159.1 ± 474.9 | 259.7 ± 102.1* | 340.9 ± 43.9** | 408.9 ± 158.9* |
| Model group | | 976.5 ± 625.9 | 168.3 ± 56.3 | 255.9 ± 42.8 | 258.1 ± 70.2 |
| Tanakan group | 0.02 | 1281.5 ± 624.1 | 224.8 ± 122.6 | 266.9 ± 109.2 | 272.4 ± 140.4 |
| Example 1 | 3 | 1947.4 ± 820.2* | 343.7 ± 162.9* | 264.3 ± 100.0 | 491.1 ± 162.4** |
| Example 2 | 3 | 1863.8 ± 688.7** | 444.5 = 327.6* | 323.8 ± 117.9 | 571.0 ± 171.0** |
| Example 5 | 3 | 1874.9 ± 574.3** | 363.6 ± 161.5* | 284.2 ± 76.1 | 472.3 ± 123.7** |
| Example 6 | 3 | 1682.6 ± 304.8* | 359.2 ± 187.2* | 306.4 ± 154.3 | 521.5 ± 67.4** |
| Example 9 | 3 | 1949.1 ± 603.7** | 489.4 ± 304.1* | 273.7 ± 79.1 | 562.0 ± 91.2** |
| Example 11 | 3 | 1751.7 ± 419.6* | 387.1 ± 270.2* | 257.6 ± 121.5 | 485.1 ± 127.3** |
| Comparative example 1 | 3 | 1437.5 ± 364.2 | 251.6 ± 220.1 | 264.8 ± 107.6 | 424.6 ± 125.7* |
| Comparative example 2 | 3 | 1572.0 ± 422.4 | 228.6 ± 165.4 | 261.2 ± 98.4 | 452.7 ± 82.2* |
| Comparative example 3 | 3 | 1420.7 ± 237.8 | 238.2 ± 151.3 | 281.2 ± 130.7 | 416.3 ± 49.1* |
| Comparative example 4 | 3 | 1253.6 ± 584.1 | 210.3 ± 116.7 | 279.3 ± 121.5 | 443.5 ± 116.3* |
| Comparative example 5 | 3 | 1137.1 ± 601.2 | 198.1 ± 143.2 | 256.5 ± 113.9 | 387.2 ± 73.2* |
| Comparative example 6 | 3 | 1221.4 ± 139.7 | 187.6 ± 219.3 | 265.4 ± 127.3 | 384.5 ± 57.1* |
| Comparative example 7 | 3 | 1474.9 ± 427.5 | 237.4 ± 152.4 | 283.1 ± 109.8 | 437.9 ± 84.3* |
| Comparative example 8 | 3 | 1057.1 ± 357.1 | 198.7 ± 133.8 | 267.2 ± 87.6 | 371.2 ± 65.8* |

PS:
Compared with the model group, *P < 0.05; **P < 0.01

Summary

Studies suggest that whether cerebral infarct can cause dementia is mainly related to the size, number and location of the infarct lesions. Investigations have showed that if the volume of the infarct lesion is larger than 50 mL, it can be combined with dementia, if the volume is greater than 100 mL, it is often combined with dementia; investigations have also found that among VaD patients, the ones with large volume of infarct lesions accounted for 11.2%, the ones with small volume of infarct lesions accounted for 88.8%, the one with multiple infarct lesions accounted for 97.6%, suggesting that small volume of lesion can also cause dementia, especially the more the number of infarct lesions, the higher the incidence of dementia. There are also studies suggest that the site of the cerebral infarction is the key factor leading to dementia; the majority of reports mentioned that the ones with periventricular white matter lesions changes in CT, the incidence of dementia significantly increased. Researches based on multi-infarct dementia (MID) model have guidance on the determination of the effectiveness of drug treatment of VaD.

Brain mechanisms of learning and memory mainly includes neurophysiological mechanisms and neurochemical mechanisms, neurophysiological mechanisms focuses on the location of the memory in the brain and the accompanying bioelectrical activity routines, neurochemical mechanism mainly explains the effects of neurotransmitters, neuropeptides and biological large molecular on learning and memory and their relations. Neuropeptide generally refers to an endogenous active substance presents in the nervous tissue and participates in the function of the nervous system, it is a kind of special information material. It is characterized in low content, high activity, broad and complex effect, regulating a wide variety of physiological functions of the body, such as pain, sleep, mood, learning and memory as well as the differentiation and development of the nervous system itself, they are all adjusted by the neuropeptide. Somatostatin (SS) is a neuroactive peptide that widely distributed in the nervous system, the highest content of SS locates in the hypothalamus and brain cortex and hippocampus, such distribution is related to its regulation of cognitive function. SS in brains have a positive regulatory role for learning and memory, the pathways for the SS to regulate learning and memory are: one, direct pathway, through the excitement of SS nerves, an increase in calcium influx is caused, and second, possibly through other nerve tracts. SS neurons and cholinergic neurons are very close, and have synapse connections, which provides evidence for their function contact: SS may promote the release of acetylcholine which affects learning and memory function. Endothelin (endothelin-1, ET) is a recent in-depth study of a vasoactive peptide, it is a neurotransmitter, and has a strong vasoconstrictor properties, widely distributed in various organs of the body, in addition to causing vasoconstriction, ET is still capable of causing direct damage to neurons and glial cells, in patients with hemorrhagic, ischemic cerebrovascular disease, the concentrations of plasma ET were significantly increased, the ET levels and the sizes of the cerebral infarct lesions have a significant positive correlation. ET acts on the nerve cells, make the nerve cells calcium overload, and generate free radicals, further aggravate brain damage. Neuropeptide Y (NPY) is an active polypeptide consisting of 36 amino acids, in the central nervous system, it is mainly located in the cerebral cortex, hippocampus, thalamus, hypothalamus and brain stem, the highest concentration of NPY is in the hippocampus, and the hippocampus is the key parts that regulate learning and memory. NPY is originally synthesized inside the nerve cells, then is transported to nerve endings and is stored in vesicles, and is coexist with the classic neurotransmitters such as norepinephrine, epinephrine, γ-aminobutyric acid and somatostatin. NPY does not only closely relate to long-term memory, but it also has an impact on short-term memory. NPY plays its biologic role primarily through its receptors, current studies suggested that, mRNA expression of Y2 receptor in hippocampus is most abundant, the adjustment of the receptors on learning and memory may be a long-transfer potentiation (LTP) mechanism. Because of the above correlation between neuropeptides and learning and memory and their correlation with cholinergic and adrenergic neurotransmitter, we examined the plasma neuropeptide and the levels of monoamine neurotransmitters of cortex, striatum, hippocampus and effects of drugs of MID model rats.

In the experiment, the microspheres were injected into the carotid artery, rat multi-infarct dementia (MID) model was created. The results showed that 24 hours later, neurobehavioral disorder appeared for model animals, multiple infarct was formed, after 10 days, liquefaction necrosis of the brain tissues of the infarct lesions happened, after 100 days, the cortex became thinner, the hippocampus atrophied, the weight of the cortex, striatum, hippocampus were significantly reduced, learning and memory impairment appeared, the contents of 5-HT, 5-HIAA of cortex and hippocampus were significantly decreased, the content of DA had a tendency to decrease but there were no significant differences (P<0.01), the content of NPY in the plasma was significantly decreased, the content of ET was significantly increased, the contents of SS and CGRP had tendencies to decrease.

30~90 days after the rats were given gavages of the Chinese medicinal compositions of the present invention (40~100 days after the models were created), compared with the model group, the time of duration of the rats of the group of the Chinese medicinal compositions of the present invention in MORRIS water maze was significantly decreased, the ability of learning and memory were significantly increased; 90 days after the administration, the weight of hippocampus was significantly increased (P<0.05), the contents of cortical 5-HT, 5-HIAA and DA, the contents of striatal 5-HT, 5-HIAA and the contents of hippocampal NE, DA, 5-HT were significantly increased (P<0.05~0.01), the contents of plasma NPY and SS were significantly increased, the contents of ET was significantly decreased. It is indicated that the content of the neurotransmitter that is related to learning and memory in the brain of MID rats can be increased by the Chinese medicinal compositions of the present invention, thus the Chinese medicinal compositions of the present invention have a therapeutic effect on vascular dementia. In addition, from the data of the comparative experiments, it can be seen that the effects of the Chinese medicinal compositions of the present invention are better than that of the Chinese medicinal compositions of the comparative examples, and the data have statistical significance.

The invention claimed is:

1. A method of preparing a Chinese medicinal composition consisting of ginseng extract, Ginkgo leaf extract, and stigma croci extract, the method comprising:
   adding ginseng, ginkgo leaf and stigma croci in weight proportions of 1:0.8-1.5:0.018-0.030,
   preparing ginseng extract, preparing ginkgo leaf extract, preparing stigma croci extract, and
   mixing the ginseng extract, the ginkgo leaf extract and the stigma croci extract to form a composition consisting of ginseng, ginkgo leaf and stigma croci.

2. The method according to claim 1, wherein in preparing ginseng extract, the main component obtained is total ginsenosides; in preparing Ginkgo leaf extract, the main component obtained is Ginkgo leaf total flavonoids and total lactones; in preparing stigma croci extract, the main component obtained is stigma croci total glycosides.

3. The method according to claim 2, wherein preparing the ginseng extract comprises:
   grinding the ginseng into powders, then subjecting the powders to reflux extraction with ethanol for 2 times and filtration, obtaining a filtrate;
   compressing the filtrate to recover a solvent until the relative density is 1.12-1.14 at 70° C.,
   adding water to the solvent in an amount that equals 2-6 times of that of crude drug and stirring homogeneously,
   cooling for precipitation, loading the supernatant onto a macroporous adsorptive resin,
   eluting the supernatant with ethanol, and
   collecting and concentrating the ethanol eluent until dry to obtain the ginseng extract;
preparing the Ginkgo leaf extract comprises:
   immersing Ginkgo leaf coarse powder with ethanol and filtering to produce a filter residue,
   immersing the filter residue with ethanol, filtering again, combining the obtained filter residues, and
   concentrating the combined filter residues under reduced pressure until the relative density is 1.12-1.14 at 70° C. to obtain a concentrated filtrate,
   adding water to the concentrated filtrate in an amount that equals 2-6 times of that of crude drug and stirring homogeneously,
   cooling for precipitation, filtering to obtain a filtrate and loading the filtrate onto a macroporous adsorptive resin,
   deluting the supernatant with ethanol, and
   collecting and concentrating the ethanol eluent until the relative density is 1.02-1.04 at 70° C.,
   extracting the concentrated eluent with ethyl acetate:n-butyl alcohol, and
   combining and compressing the extracts to recover solvent to obtain Ginkgo leaf extract; and
preparing the stigma croci extract comprises:
   immersing stigma croci crude drug into and filtering to obtain residues,
   immersing the residues in ethanol and filtering to produce filtrates,
   combining the obtained filtrates, concentrating the combined filtrates under reduced pressure until the relative density is 1.12-1.14 at 70° C.,
   adding water to the concentrated filtrates to obtain a concentrated filtrate solution and loading the concentrated filtrate solution onto a macroporous adsorptive resin,
   eluting with ethanol, concentrating the ethanol eluent, wherein it is concentrated until dry to obtain stigma croci extract, the stigma croci extract having a relative density of 1.02-1.04 at 70° C.

4. The method according to claim 1, wherein the ginseng, ginkgo leaf and stigma croci are added in weight proportions of 1:1:0.018-0.030.

5. The method according to claim 1, the ginseng, ginkgo leaf and stigma croci are added in weight proportions of 1:0.9-1.2:0.020-0.025.

6. The method according to claim 1, wherein the ginseng, ginkgo leaf and stigma croci are added in weight proportions of 1:1:0.020-0.025.

7. The method according to claim 1, wherein the ginseng, ginkgo leaf and stigma croci are added in weight proportions of 1:1:0.022.

\* \* \* \* \*